US012661497B2

(12) United States Patent
Ratz et al.

(10) Patent No.: US 12,661,497 B2
(45) Date of Patent: Jun. 23, 2026

(54) INTRA-CARDIAC LEFT ATRIAL AND DUAL SUPPORT SYSTEMS

(71) Applicant: inQB8 Medical Technologies, LLC, Winchester, MA (US)

(72) Inventors: J. Brent Ratz, Winchester, MA (US); Arshad Quadri, West Hartford, CT (US)

(73) Assignee: inQB8 Medical Technologies, LLC, Winchester, MA (US)

( * ) Notice: Subject to any disclaimer, the term of this patent is extended or adjusted under 35 U.S.C. 154(b) by 35 days.

(21) Appl. No.: 18/400,284

(22) Filed: Dec. 29, 2023

(65) Prior Publication Data
US 2024/0207598 A1     Jun. 27, 2024

Related U.S. Application Data

(63) Continuation of application No. 17/144,706, filed on Jan. 8, 2021, now Pat. No. 11,883,640, which is a
(Continued)

(51) Int. Cl.
*A61M 60/148*     (2021.01)
*A61B 5/318*     (2021.01)
(Continued)

(52) U.S. Cl.
CPC ........... *A61M 60/148* (2021.01); *A61B 5/318* (2021.01); *A61M 60/17* (2021.01);
(Continued)

(58) Field of Classification Search
CPC .. A61M 1/107; A61M 1/1072; A61M 1/1074; A61M 1/122; A61M 2205/3331
See application file for complete search history.

(56) References Cited

U.S. PATENT DOCUMENTS

| | | | |
|---|---|---|---|
| 3,421,497 | A | 1/1969 | Chesnut et al. |
| 3,505,987 | A | 4/1970 | Heilman |

(Continued)

FOREIGN PATENT DOCUMENTS

| | | |
|---|---|---|
| CN | 1268894 A | 10/2000 |
| EP | 0192574 A1 | 8/1986 |

(Continued)

OTHER PUBLICATIONS

Emoto et al., Intra-Right-Atrial Balloon Pumping (IRABP) During a Fontan Procedure, ASAIO Transactions, Harper and Row Publishers, Hagerstown, MD, US, vol. 33. No. 3, Sep. 1, 1987, pp. 699-703.

(Continued)

*Primary Examiner* — Joseph M Dietrich
(74) *Attorney, Agent, or Firm* — Knobbe, Martens, Olson & Bear, LLP

(57) ABSTRACT

A system for treating atrial dysfunction, including heart failure and/or atrial fibrillation, that includes one or more pressurizing elements and control circuitry. The one or more pressurizing elements can comprise one or more balloons and can be configured to be positioned in the left atrium, and optionally the pulmonary artery, of a patient's heart. The one or more pressurizing elements can be coupled to one or more positioning structures that can be configured to position the one or more pressurizing elements in the left atrium, and optionally the pulmonary artery. The control circuitry can be configured to operate the one or more pressurizing elements to decrease or increase pressure and/or volume in the left atrium, and optionally the pulmonary artery, in accordance with different phases of the cardiac cycle. The control circuitry can be further configured to operate the one or more pressurizing elements to generate coordinated pressure
(Continued)

600 ⌐ modifications in the left atrium, and optionally the pulmonary artery.

20 Claims, 15 Drawing Sheets

Related U.S. Application Data continuation of application No. 16/782,997, filed on Feb. 5, 2020, now Pat. No. 10,888,644.

(60) Provisional application No. 62/801,917, filed on Feb. 6, 2019, provisional application No. 62/801,819, filed on Feb. 6, 2019.

(51) Int. Cl.

| | |
|---|---|
| *A61M 60/17* | (2021.01) |
| *A61M 60/237* | (2021.01) |
| *A61M 60/295* | (2021.01) |
| *A61M 60/497* | (2021.01) |
| *A61M 60/515* | (2021.01) |
| *A61M 60/531* | (2021.01) |
| *A61M 60/538* | (2021.01) |
| *A61M 60/843* | (2021.01) |
| *A61M 60/861* | (2021.01) |

(52) U.S. Cl.
CPC ........ *A61M 60/237* (2021.01); *A61M 60/295* (2021.01); *A61M 60/497* (2021.01); *A61M 60/515* (2021.01); *A61M 60/531* (2021.01); *A61M 60/538* (2021.01); *A61M 60/843* (2021.01); *A61M 60/861* (2021.01); *A61M 2205/3331* (2013.01)

(56) References Cited

U.S. PATENT DOCUMENTS

| | | | |
|---|---|---|---|
| 4,080,958 A | 3/1978 | Bregman et al. | |
| 4,407,271 A | 10/1983 | Schiff | |
| 4,522,195 A | 6/1985 | Schiff | |
| 4,685,446 A | 8/1987 | Choy | |
| 4,697,574 A | 10/1987 | Karcher et al. | |
| 4,861,330 A | 8/1989 | Voss | |
| 4,877,035 A | 10/1989 | Bogen et al. | |
| 4,902,273 A | 2/1990 | Choy et al. | |
| 5,098,370 A | 3/1992 | Rahat et al. | |
| 5,129,878 A | 7/1992 | Takano et al. | |
| 5,344,385 A | 9/1994 | Buck et al. | |
| 5,449,342 A | 9/1995 | Hirose et al. | |
| 5,613,946 A | 3/1997 | Mckeever | |
| 5,820,542 A | 10/1998 | Dobak, III et al. | |
| 6,191,111 B1 | 2/2001 | Leschinsky | |
| 6,468,200 B1 | 10/2002 | Fischi | |
| 6,544,216 B1* | 4/2003 | Sammler | A61M 60/13 |
| | | | 604/95.03 |
| 6,572,652 B2 | 6/2003 | Shakinovich | |
| 6,942,611 B2 | 9/2005 | Siess | |
| 7,204,798 B2 | 4/2007 | Zdeblick et al. | |
| 7,374,531 B1 | 5/2008 | Kantrowitz | |
| 7,468,050 B1 | 12/2008 | Kantrowitz | |
| 9,017,359 B2 | 4/2015 | Scandurra et al. | |
| 10,500,038 B1 | 12/2019 | Orlov et al. | |
| 10,561,773 B2 | 2/2020 | Ferrari et al. | |
| 10,888,644 B2 | 1/2021 | Ratz et al. | |
| 11,883,640 B2 | 1/2024 | Ratz et al. | |
| 2002/0026233 A1 | 2/2002 | Shaknovich | |
| 2002/0169413 A1 | 11/2002 | Keren et al. | |
| 2002/0198436 A1 | 12/2002 | Hoshino | |
| 2003/0070683 A1 | 4/2003 | Deem et al. | |
| 2003/0135086 A1 | 7/2003 | Khaw et al. | |
| 2004/0054251 A1 | 3/2004 | Liotta | |
| 2004/0127982 A1 | 7/2004 | Machold et al. | |

| | | | |
|---|---|---|---|
| 2004/0243122 A1 | 12/2004 | Auth et al. | |
| 2005/0273160 A1 | 12/2005 | Lashinski et al. | |
| 2006/0020334 A1 | 1/2006 | Lashinski et al. | |
| 2006/0047205 A1 | 3/2006 | Ludomirsky et al. | |
| 2006/0252977 A1 | 11/2006 | Sullivan | |
| 2006/0271173 A1 | 11/2006 | Delgado, III et al. | |
| 2007/0162102 A1 | 7/2007 | Ryan et al. | |
| 2007/0219630 A1 | 9/2007 | Chu | |
| 2007/0287880 A1 | 12/2007 | Ovil et al. | |
| 2008/0004485 A1 | 1/2008 | Moreschi | |
| 2008/0071135 A1 | 3/2008 | Shaknovich | |
| 2010/0010623 A1 | 1/2010 | Lashinski et al. | |
| 2011/0130619 A1 | 6/2011 | Whisenant et al. | |
| 2011/0218478 A1 | 9/2011 | Keren et al. | |
| 2011/0218479 A1 | 9/2011 | Rottenberg et al. | |
| 2012/0203147 A1 | 8/2012 | Lurie et al. | |
| 2012/0259263 A1 | 10/2012 | Celermajer et al. | |
| 2012/0296153 A1 | 11/2012 | Laufer et al. | |
| 2013/0289717 A1 | 10/2013 | Solem | |
| 2014/0012181 A1 | 1/2014 | Sugimoto et al. | |
| 2015/0039076 A1 | 2/2015 | Park | |
| 2015/0148731 A1 | 5/2015 | McNamara et al. | |
| 2015/0202403 A1 | 7/2015 | Lurie et al. | |
| 2016/0089482 A1 | 3/2016 | Siegenthaler | |
| 2016/0324636 A1 | 11/2016 | Rourke et al. | |
| 2016/0374657 A1 | 12/2016 | Kreidler | |
| 2017/0079790 A1 | 3/2017 | Vidlund et al. | |
| 2017/0333607 A1* | 11/2017 | Zarins | A61M 60/857 |
| 2018/0008408 A1 | 1/2018 | Solem | |
| 2018/0104491 A1 | 4/2018 | Lerner | |
| 2018/0132999 A1 | 5/2018 | Perouse | |
| 2018/0133011 A1 | 5/2018 | Perouse | |
| 2019/0167429 A1 | 6/2019 | Stearns et al. | |
| 2020/0397569 A1 | 12/2020 | Yildirim et al. | |
| 2022/0280768 A1 | 9/2022 | Heilmann et al. | |
| 2023/0036909 A1 | 2/2023 | Quadri et al. | |

FOREIGN PATENT DOCUMENTS

| | | |
|---|---|---|
| EP | 0238791 A2 | 9/1987 |
| EP | 0842673 A1 | 5/1998 |
| EP | 0808191 B1 | 10/2002 |
| EP | 1276520 A1 | 1/2003 |
| EP | 0706343 B1 | 10/2003 |
| EP | 1021218 B1 | 12/2003 |
| EP | 1066066 B1 | 7/2004 |
| EP | 1502554 A2 | 2/2005 |
| EP | 1051168 B1 | 3/2006 |
| EP | 1313410 B1 | 5/2007 |
| EP | 0989826 A1 | 10/2007 |
| EP | 1443880 B1 | 3/2010 |
| EP | 1180045 B1 | 3/2012 |
| EP | 2231069 B1 | 4/2012 |
| EP | 1796597 B1 | 1/2013 |
| EP | 2564771 A1 | 3/2013 |
| EP | 2477555 B1 | 12/2013 |
| EP | 1804860 B1 | 4/2014 |
| EP | 2097536 B1 | 7/2014 |
| EP | 2211936 B1 | 7/2014 |
| EP | 2549956 B1 | 10/2014 |
| EP | 2195043 B1 | 12/2014 |
| EP | 2870978 A1 | 5/2015 |
| EP | 2217302 A1 | 9/2015 |
| EP | 1748745 B1 | 12/2015 |
| EP | 3000437 A1 | 3/2016 |
| EP | 3017792 A1 | 5/2016 |
| EP | 2410948 B1 | 7/2016 |
| EP | 3141185 A1 | 3/2017 |
| EP | 2673038 B1 | 7/2017 |
| EP | 3275389 A1 | 1/2018 |
| EP | 1945112 B1 | 5/2018 |
| EP | 2948099 B1 | 5/2018 |
| EP | 1771132 B1 | 3/2019 |
| EP | 1855623 B1 | 4/2019 |
| EP | 3473279 A1 | 4/2019 |
| EP | 2376011 B1 | 7/2019 |
| EP | 2429603 B1 | 9/2019 |
| EP | 2203213 B1 | 10/2019 |
| EP | 3651826 A1 | 5/2020 |

(56)  References Cited

FOREIGN PATENT DOCUMENTS

| | | | |
|---|---|---|---|
| JP | 2004-507317 | A | 3/2004 |
| JP | 2006-518249 | A | 3/2007 |
| JP | 2007-536003 | A | 12/2007 |
| JP | 2014-502860 | A | 2/2014 |
| WO | WO 1995/028974 | A1 | 11/1995 |
| WO | WO 98/56291 | A1 | 12/1998 |
| WO | WO 99/59652 | A1 | 11/1999 |
| WO | WO 2001/003753 | A1 | 1/2001 |
| WO | WO 2001/036035 | A1 | 5/2001 |
| WO | WO 02/17819 | A2 | 3/2002 |
| WO | WO 03/049619 | A2 | 6/2003 |
| WO | WO 2003/059209 | A2 | 7/2003 |
| WO | WO 03/068292 | A1 | 8/2003 |
| WO | WO 2003/082379 | A1 | 10/2003 |
| WO | WO 03/103534 | A2 | 12/2003 |
| WO | WO 2004/043516 | A2 | 5/2004 |
| WO | WO 2004/069055 | A2 | 8/2004 |
| WO | WO 2004/073484 | A2 | 9/2004 |
| WO | WO 2004/078234 | A2 | 9/2004 |
| WO | WO 2004/066817 | A2 | 12/2004 |
| WO | WO 2005/027753 | A1 | 3/2005 |
| WO | WO 2005/037345 | A3 | 4/2005 |
| WO | WO 2005/074384 | A2 | 8/2005 |
| WO | WO 2006/042280 | A3 | 4/2006 |
| WO | WO 2007/025028 | A1 | 3/2007 |
| WO | WO 2007/029252 | A2 | 3/2007 |
| WO | WO 2008/005747 | A2 | 1/2008 |
| WO | WO 2008/045265 | A2 | 4/2008 |
| WO | WO 2008/055301 | A1 | 5/2008 |
| WO | WO 2008/079828 | A3 | 7/2008 |
| WO | WO 2008/121888 | A1 | 10/2008 |
| WO | WO 2009/092782 | A1 | 7/2009 |
| WO | WO 2009/137530 | A3 | 11/2009 |
| WO | WO 2009/152297 | A1 | 12/2009 |
| WO | WO 2010/148412 | A1 | 12/2010 |
| WO | WO 2011/056823 | A2 | 5/2011 |
| WO | WO 2011/156714 | A2 | 12/2011 |
| WO | WO 2012/071395 | A1 | 5/2012 |
| WO | WO 2012/075279 | A1 | 6/2012 |
| WO | WO 2012/145167 | A2 | 10/2012 |
| WO | WO 2013/059743 | A1 | 4/2013 |
| WO | WO 2013/059747 | A1 | 4/2013 |
| WO | WO 2013/096965 | A1 | 6/2013 |
| WO | WO 2013/123059 | A1 | 8/2013 |
| WO | WO 2014/114798 | A1 | 7/2014 |
| WO | WO 2014/153544 | A1 | 9/2014 |
| WO | WO 2014/160330 | A1 | 10/2014 |
| WO | WO 2014/201452 | A1 | 12/2014 |
| WO | WO 2015/085119 | A1 | 6/2015 |
| WO | WO 2015/109243 | A1 | 7/2015 |
| WO | WO 2016/016899 | A1 | 2/2016 |
| WO | WO 2016/126921 | A1 | 8/2016 |
| WO | WO 2016/134239 | A1 | 8/2016 |
| WO | WO 2016/178136 | A1 | 11/2016 |
| WO | WO 2017031068 | A1 | 2/2017 |
| WO | WO 2017/035381 | A1 | 3/2017 |
| WO | WO 2017/062858 | A1 | 4/2017 |
| WO | WO 2017/064321 | A1 | 4/2017 |
| WO | WO 2017/151566 | A1 | 9/2017 |
| WO | WO 2017/202766 | A3 | 11/2017 |
| WO | WO 2018/106569 | A1 | 4/2018 |
| WO | WO 2018/148456 | A1 | 8/2018 |
| WO | WO 2018/165225 | A1 | 9/2018 |
| WO | WO 2018/178966 | A1 | 10/2018 |
| WO | WO 2019/051213 | A1 | 3/2019 |
| WO | WO 2019/052610 | A1 | 3/2019 |
| WO | WO 2019/055154 | A2 | 3/2019 |
| WO | WO 2019/099722 | A2 | 5/2019 |
| WO | WO 2019/109013 | A1 | 6/2019 |
| WO | WO 2019/112983 | A1 | 6/2019 |
| WO | WO 2019/112985 | A1 | 6/2019 |
| WO | WO 2019/113011 | A1 | 6/2019 |
| WO | WO 2019/136040 | A1 | 7/2019 |
| WO | WO 2019/165213 | A1 | 8/2019 |
| WO | WO 2019/244031 | A1 | 12/2019 |
| WO | WO 2020/005551 | A1 | 1/2020 |
| WO | WO 2020/010144 | A1 | 1/2020 |
| WO | WO 2020/117888 | A1 | 6/2020 |
| WO | WO 2020/163504 | A1 | 8/2020 |
| WO | WO 2021/138502 | A1 | 7/2021 |

OTHER PUBLICATIONS

International Search Report and Written Opinion in PCT/US2020/016848, mailed on May 29, 2020, in 25 pages.
International Preliminary Report on Patentability in PCT/US2020/016848, mailed on Aug. 10, 2021 in 16 pages.
International Search Report and Written Opinion in PCT/US2020/067580, mailed on Jun. 9, 2021, in 13 pages.
International Preliminary Report on Patentability in PCT/US2020/067580, mailed on Jul. 14, 2022, in 7 pages.

* cited by examiner

100

102

106

101

110

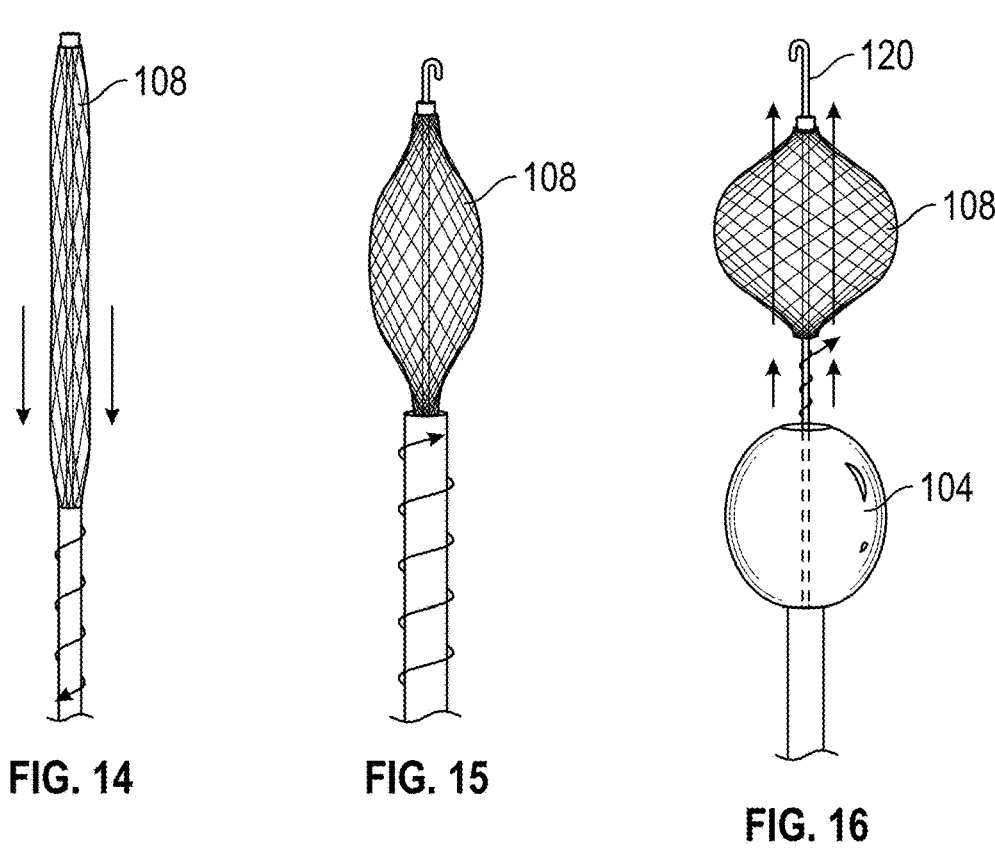
FIG. 14          FIG. 15
FIG. 16
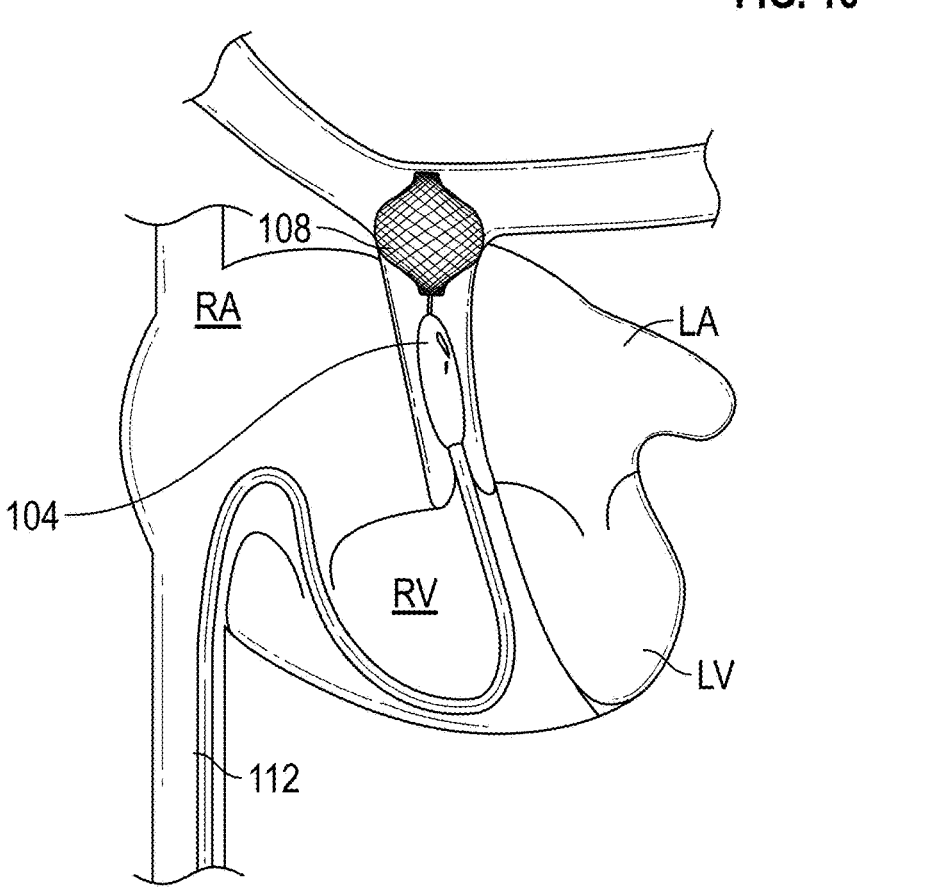
FIG. 17

1702A

INTRA-CARDIAC LEFT ATRIAL AND DUAL SUPPORT SYSTEMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field of the Invention

The present disclosure generally relates to implantable cardiac devices and, more particularly, to intra-cardiac left atrial support systems and intra-cardiac dual support systems.

Description of the Related Art

Heart Failure (HF) is a common problem throughout the world and affects more than 6.5 million people in the United States alone, a number that is expected to increase to nearly 8.5 milling by 2030. While many of these patients are able to live asymptomatically with chronic HF, every year 1.8M patients experience Acute Heart Failure (AHF), a rapid worsening of heart failure symptoms, primarily including dyspnea and fatigue, which requires urgent treatment and immediate hospitalization. In addition to the impact it has on the quality of life for these patients, HF treatments and hospitalizations cost the U.S. healthcare system over $30B annually. AHF is generally split between two classifications, Heart Failure with reduced Ejection Fraction (HFrEF, also referred to as systolic HF) and Heart Failure with preserved Ejection Fraction (HFpEF, also referred to as diastolic HF). While both HFrEF and HFpEF are associated with significant impacts on morbidity and mortality, HFpEF has proven more difficult to address, and despite numerous efforts to develop therapeutic treatments for the disease, diuretics remain one of the only evidence based therapies to placate the effects of HFpEF. As such, in addition to opportunities for improved solutions for HFrEF and Atrial Fibrillation (AF), there is a significant unmet clinical need to develop a meaningful therapeutic solution for patients suffering from HFpEF.

At a certain point in the mechanistic and physiological progression of HF, Left Atrial dysfunction begins to take place. The walls of the Left Atrium (LA) become stiffer and less compliant leading to a reduction in Left Atrial reservoir strain (expansion during filling) and active strain (compression during emptying). This reduction in strain drives increased pressure in the Left Atrium which propagates to the lungs (measured by an increase in Pulmonary Capillary Wedge Pressure (PCWP)), reducing lung gas diffusion (measured by diffusion of the lungs for carbon monoxide (DLCO) and arterial and mixed blood gases), which is the fundamental driver of pulmonary congestion and dyspnea, leading to AHF and hospitalization.

In treating HFrEF, the issue resides with the compromised systolic function of the Left Ventricle (LV). As a result, several therapies have been developed to assist the left ventricle in generating systemic pressure and systolic flow to support cardiac output (e.g. LVADs). However, since the systolic function and ejection fraction are preserved with HFpEF, the transference of HFrEF therapies is not well suited or effective.

Research performed in the last several years has highlighted the role of the LA and Left Atrial Pressure in HFpEF. More specifically, research has identified Left Atrial dysfunction (e.g., reduced Left Atrial Reservoir and Active strains) as an independent risk factor associated with HFpEF mortality.

FIG. 1A shows the LA pressure and volume wave forms, which can be combined to depict a "figure-eight" pressure: volume relationship (FIG. 1B).

The expansion of the LA during atrial diastole (through ventricular systole) is known as the reservoir function and is represented by the segments labeled (1) in FIGS. 1A and 1B. Once the mitral valve opens in early diastole, LA and LV pressures equalize and blood passively empties into the LV. This is known as the conduit function and is represented by segment (2) in FIGS. 1A and 1B. Then, at the end of diastole, just before the mitral valve closes, the atrium contracts serving the active pump function represented by segments (4) and (5) in FIGS. 1A and 1B.

In the presence of Congestive Heart Failure (CHF) the normal "figure-eight" illustrated in FIG. 1B is driven up and to the right as LA dilation and volume increase is coupled with increasing stiffness and higher pressures. The increased stiffness also changes the shape of the curves and reduces reservoir strain (reduced expansion during filling) and pump strain (compression during the atrial systole).

While HFpEF is initially associated with increased LV diastolic filling pressures, and the inability to fully evacuate the LA, the resulting fluid backup often results in pulmonary congestion and can translate to pulmonary hypertension, RV-to-PC (Right Ventricle-pulmonary circulation) uncoupling, and right ventricular overload or dysfunction. Consequently, what begins as left-sided heart failure can often progress to right-sided heart failure. Right-sided affects may be observed as an increase in Pulmonary Vascular Resistance (PVR), Pulmonary Artery (PA) systolic pressure (which is equivalent to RV systolic pressure), increased RV workload and inefficiency, and reduced Cardiac Output. Increased LA pressure translates to increased pulmonary artery wedge pressure and increased PVR. This results in increased PA systolic pressure and reduced cardiac output during PA diastole due to a decrease in pressure differential. The increased PA systolic pressure translates to higher workload for the RV during systole and a reduction in efficiency over time.

In response to the role of elevated LA pressure in exacerbating HFpEF symptoms, intra-atrial devices can be provided that attempt to shunt blood from the LA to the Right Atrium (RA) and thereby reduce LA pressure and PCWP. Early clinic studies have shown promising results, but LA shunting does not fully address congestion in the lungs nor does it help to alleviate the burden on the right side of the heart. Instead, the RA now has to deal with increased volume due to the shunting of the blood from the left side. Furthermore, reducing pressure in the LA alone does not address the underlying atrial stiffness and does not help to restore the complete functionality of the LA in all phases of the cardiac cycle. As an example, reducing LA pressure during the active phase of atrial systole does not generate a larger pressure differential between the LA and the LV. As a result LV End Diastolic filling is not optimized and Cardiac Output is likely to be reduced since volume is being shunted to the right side instead. In addition, LA shunting may not be as effective in patients suffering from Atrial Fibrillation (AF), which is a common condition in HFpEF patients.

SUMMARY OF THE INVENTION

In some aspects of the disclosure, a system for treating atrial dysfunction is disclosed that comprises a pressurizing element and control circuitry. The pressurizing element can be configured to be positioned in a left atrium of a heart of a patient. The control circuitry can be configured to operate the pressurizing element to decrease a pressure in the left atrium during atrial diastole to draw oxygenated blood out of the lungs of the patient by increasing a relative volume of the left atrium to reduce a filling pressure in the left atrium and operate the pressurizing element to increase the pressure in the left atrium during atrial systole by reducing the relative volume of the left atrium to increase a left atrial pressure during atrial systole. The increase in the left atrial pressure during atrial systole increases a pressure differential between the left atrium and a left ventricle that improves diastolic filling of the left ventricle.

In some aspects, the system can further comprise an atrial positioning structure coupled to the pressurizing element and configured to position the pressurizing element in the left atrium. The atrial positioning structure can comprise a septal anchor or a left atrial appendage anchor. The atrial positioning structure can comprise a shaft configured to extend transseptally between a right atrium and the left atrium of the heart of the patient. The shaft can be pre-shaped with a curve or bend to facilitate positioning of the pressurizing element in the left atrium. In some aspects, the system can further comprise a shaped stylet configured to be delivered through the shaft to facilitate positioning of the pressurizing element in the left atrium.

In some aspects, the pressurizing element can comprise a balloon. Operating the pressurizing element to increase the pressure in the left atrium can comprise filling the balloon with a liquid or a gas and operating the pressurizing element to decrease the pressure in the left atrium can comprise removing the liquid or the gas from the balloon. The distal end of the balloon can be recessed within the balloon such that the distal end of the balloon is atraumatic. The balloon can comprise an open central lumen. In some aspects, the system can further comprise pressurizing components that include a pressure chamber and at least one pump disposed between the balloon and the pressure chamber. The pressurizing components can be configured to be external fixed, external ambulatory, or implantable components.

In some aspects, the atrial positioning structure can comprise a septal anchor. The septal anchor can comprise first and second expandable members configured to expand respectively against left and right sides of an atrial septum of the heart of the patient and the pressurizing element can be attached to the first expandable member.

In some aspects, the pressurizing element configured to be positioned in the left atrium can be a first pressurizing element. The system can further comprise a second pressurizing element that can be configured to be positioned in a pulmonary artery of the patient. The second pressurizing element can be coupled to a pulmonary artery positioning structure and the pulmonary artery positioning structure can be configured to position the second pressurizing element in the pulmonary artery of the patient. The control circuitry can further be configured to operate the first and second pressurizing elements to generate coordinated pressure modifications in the left atrium and the pulmonary artery. The first pressurizing element can comprise a first balloon and the second pressurizing element can comprise a second balloon.

In some aspects, a method for treating atrial dysfunction is disclosed. The method can comprise: delivering a pressurizing element into a left atrium of a patient; operating the pressurizing element to decrease a pressure in the left atrium during atrial diastole to draw oxygenated blood out of the lungs of the patient by increasing a relative volume of the left atrium to reduce a filling pressure in the left atrium; and operating the pressurizing element to increase the pressure in the left atrium during atrial systole by reducing the relative volume of the left atrium to increase a left atrial pressure during atrial systole, wherein the increase in the left atrial pressure during atrial systole increases a pressure differential between the left atrium and left ventricle that improves diastolic filling of the left ventricle.

The method of the preceding paragraph can also include one or more of the following features. The pressurizing element can be a balloon. The method can further comprise: receiving, at control circuitry from a sensor communicatively coupled to the patient, a signal corresponding to a cardiac cycle for the heart of the patient; operating the pressurizing element to decrease a pressure in the left atrium responsive to a portion of the signal; and operating the pressurizing element to increase a pressure in the left atrium responsive to an additional portion of the signal. The sensor can comprise an electrical sensor or a pressure sensor. The method can further comprise anchoring the pressurizing element within the left atrium. The pressurizing element delivered into the left atrium can be a first pressurizing element, and the method can further comprise: delivering a second pressurizing element into a pulmonary artery of the patient; operating the second pressurizing element to decrease a pressure in the pulmonary artery during pulmonary artery systole to reduce pulmonary artery systolic pressures and reduce a work load of a right ventricle of the heart of the patient; and operating the second pressurizing element to increase a pressure in the pulmonary artery during pulmonary artery diastole after a pulmonary valve is closed to increase pulmonary artery diastolic pressure to overcome pulmonary vascular resistance and increase cardiac output.

In accordance with certain aspects of the disclosure, a system is provided with an implantable fluid displacing element (e.g., a balloon, a turbine, a pump, or other pressurizing element) that can be operated to support left atrial operations during various portions of the cardiac cycle. The pressurizing element can be percutaneously positioned and anchored into the left atrium of the heart of a patient. The implantable pressurizing element is operable to support the functionality of the heart through volume displacement and pressure regulation using a variety of programmable timing schemes.

In accordance with certain aspects of the disclosure, a system is provided with two implantable fluid displacing elements (e.g., balloons, turbines, pumps, or other pressurizing elements) that can be operated in coordination to produce forward and/or backwards flow (e.g., by generating pressures and vacuums) during various portions of the cardiac cycle. The two pressurizing elements can be percutaneously positioned and anchored into two separate locations within the heart and/or vasculature of a patient. The two implantable pressurizing elements are operable and/or programmable to function together or independently with synchronous timing (e.g., in the case of balloons: both inflated, both deflated), exact inverse timing (e.g., for balloons: one inflated while the other is deflated, or for an axial pump: one forward while the other is backwards) or asynchronously with leading or lagging timing between the two different elements in order to support the functionality of the heart through volume displacement and pressure regulation using a variety of programmable timing schemes.

BRIEF DESCRIPTION OF THE DRAWINGS

FIGS. 14-16 illustrate various states of expansion for a pulmonary artery positioning structure in accordance with various aspects of the subject technology.

FIG. 17 illustrates an implanted pulmonary artery positioning structure in accordance with various aspects of the subject technology.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Aspects of this disclosure are directed to systems and methods for atrial dysfunction, including heart failure and/or atrial fibrillation. It should be appreciated that, although the use of systems such as systems 100, 600 are described below for HF applications, the systems can also be suitable for treatment of non-HF, AF patients based on its ability to restore native LA function and pulsation. Today, it is common to treat AF through ablation procedures, often referred to as maze procedures, whereby the physician uses small incisions, radio waves, freezing, microwave or ultrasound energy to create scar tissue that disrupts the electrical circuitry within the LA in an effort to eliminate the fibrillation. This is often effective via surgery but less effective when done using the currently available interventional techniques. Insufficient ablation could lead to persistent AF while over ablation could lead to scarring that causes the LA walls to stiffen and can ultimately lead to HF. By contrast, using LA balloon 102 as described below to restore LA function (expansion and contraction) could eliminate the symptoms of AF even in the presence of electrical fluctuations and without the need for ablation that could cause excessive scarring.

Left Atrial Cardiac Support System

Figure 1A:
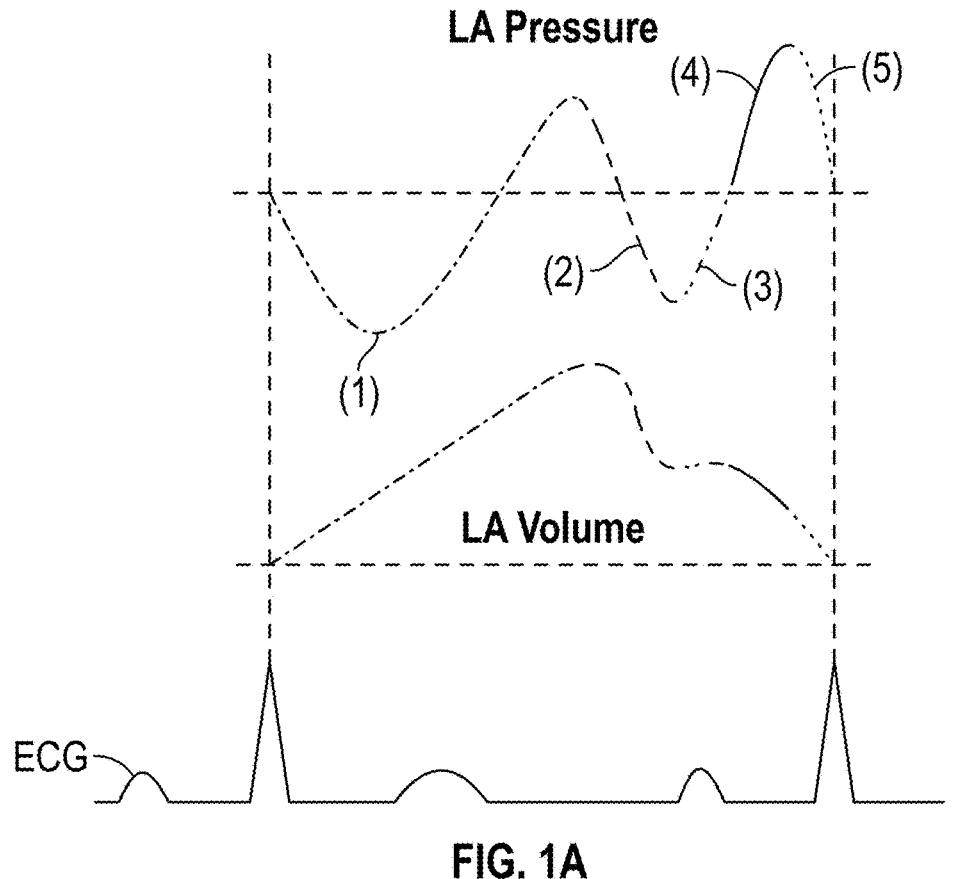
FIGS. 1A-1B illustrate the five phases in the left atrial pressure-volume relationship.
Figure 1B:
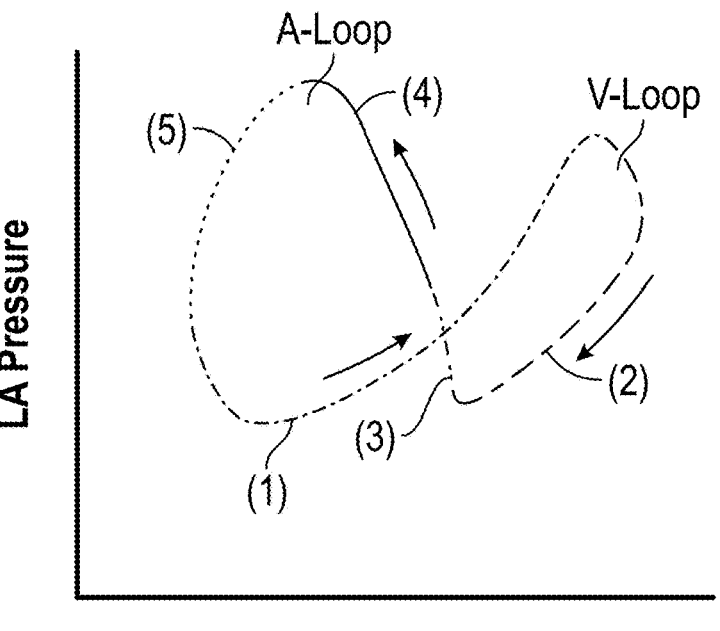
Figure 2:
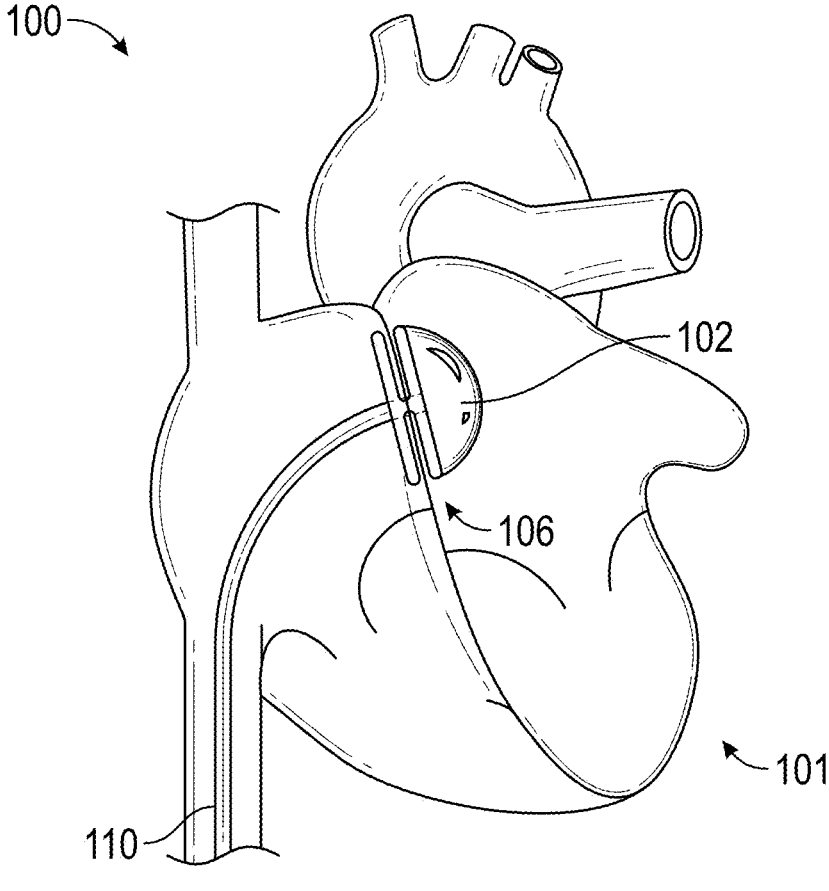
FIG. 2 illustrates a left atrial cardiac support system according to certain aspects of the present disclosure.

FIG. 2 illustrates an example system 100 in which an implantable pressurizing element has been implanted in the patient. In the example of FIG. 2, system 100 includes a pressurizing element 102 implemented as a balloon for illustrative purposes. As shown, an atrial positioning structure 106 is coupled to the pressurizing element 102 and configured to position the pressurizing element 102 in a Left Atrium LA of a heart 101 of a patient. Although not visible in FIG. 2, system 100 also includes control circuitry configured to operate the pressurizing element 102 to decrease a pressure in the Left Atrium during atrial diastole to draw oxygenated blood out of the lungs of the patient by simulating an increase in left atrial reservoir strain and a relative increase in the volume of the Left Atrium to reduce a filling pressure in the Left Atrium. The control circuitry also operates the pressurizing element 102 to increase the pressure in the Left Atrium during atrial systole to simulate an increase left atrial active strain by reducing the relative volume of the Left Atrium to increase left atrial pressure during atrial systole. The increase in the left atrial pressure during atrial systole increases a pressure differential between the Left Atrium and Left Ventricle that improves diastolic filling of the Left Ventricle.

A feed line 110 is shown, through which a fluid or a gas can be provided or removed for inflation or deflation of balloon implementations of pressurizing element 102, or with which control signals can be provided for operation of other implementations of pressurizing element 102. The feed line 110 may be incorporated into or be part of an elongate catheter body used to deliver the pressurizing element 102 to the Left Atrium LA. For example, in both balloon and non-balloon embodiments, in some aspects a catheter or sheath may be delivered in a percutaneous approach through the femoral vein and advanced through the inferior vena cava, to the Right Atrium RA, and across the atrial septum into the Left Atrium LA. The pressurizing element 102 is positioned at a distal end of the elongate body and may be expanded in the LA. An expandable atrial positioning structure 106, shown proximal to the balloon in FIG. 2, may expand on the left and/or right sides of the septum to help secure the balloon within the LA. In some embodiments, the catheter body carrying the balloon may be delivered through a separate trans-septal sheath that is positioned between the RA and LA.

System 100 may also include one or more sensors such as electrocardiogram (ECG) sensors and/or pressure sensors that generate signals that correspond to portions of the cardiac cycle of the patient. Pressurizing element 102 can be operated to generate pressure changes (e.g., pressure increases and/or pressure decreases) in the Left Atrium, in coordination with various portions of the cardiac cycle based on the signals from the sensor.

In accordance with aspects of the present disclosure, the left-atrial support system 100 of FIG. 2 is provided to address potential dysfunction on the left side of the heart, potentially before problems occur on the right side and/or to alleviate dysfunction on both sides of the heart via reducing pulmonary capillary wedge pressure (a proxy for pulmonary congestion) and improved filling of the Left Ventricle.

In contrast with HFpEF treatments with devices that reduce LA pressure only at the cost of increasing the burden on the right side of the heart and decreasing cardiac output, systems 100 as described herein support the heart by reducing the burden on the left side of the heart without adding burden to the right atrium, thereby potentially also reducing congestion and pulmonary wedge pressure and improving LV diastolic filling, which can provide a net increase in cardiac output. This is achieved by placing a fluid/volume displacing system on the left side of the heart (e.g., pressurizing element 102 in the Left Atrium). In the example discussed herein in which pressurizing element 102 is implemented as a balloon, the inflation and deflation of the balloon is timed in such a way to optimize support for each patient and keep blood moving in the proper direction at all times during the cardiac cycle.

Deflation of a balloon 102 in the Left Atrium during atrial diastole can help draw oxygenated blood out of the lungs by simulating an increase in LA reservoir strain (e.g., increase in volume during filling) and increasing the relative volume of the LA and reducing the filling pressures. Then, by inflating balloon 102 during the active portion of the diastolic cycle (e.g., during atrial systole) the balloon can simulate an increase in pump/active strain by reducing the relative volume in the LA and increasing LA pressure during the active phase of the cycle, thereby increasing the LA-to-LV pressure differential and improving diastolic filling of the Left Ventricle. This operation of LA balloon 102 serves to restore compliance to areas of the heart (e.g., the LA and LV) that are experiencing increased stiffness and wall stress.

In various operational scenarios, balloon 102 (or other implementations of the pressurizing element for fluid/volume displacement in the LA) can be operated depending on the placement of the balloon and the specific needs of each patient.

Inflation and deflation of balloon 102 can be based on an initial (e.g., fixed) timing or can be triggered by sensor signals from electrocardiogram (e.g., EKG or ECG) sensors, pressure sensors (e.g., a pressure sensor in or near the LA), or a combination thereof.

Figure 3:
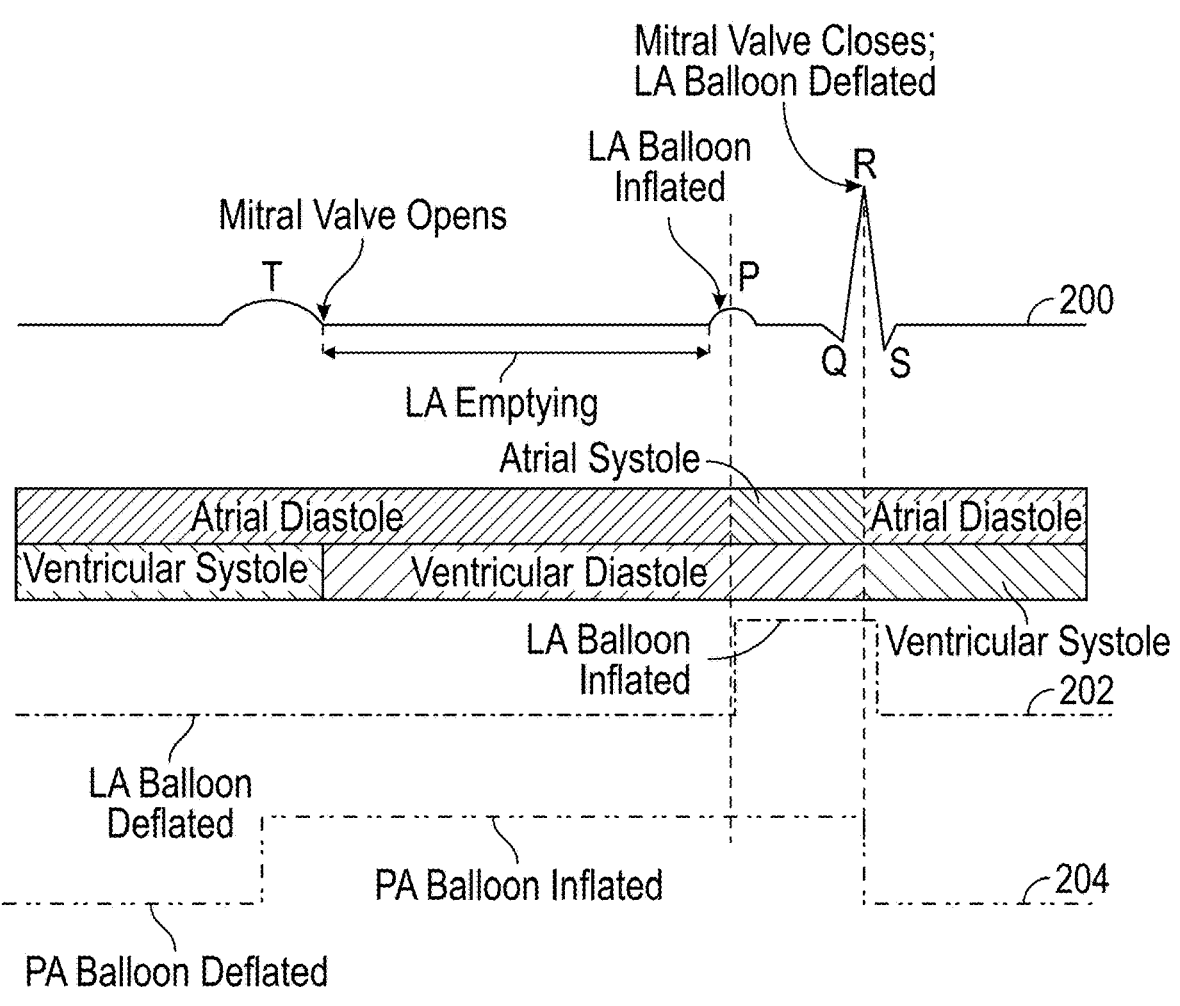
FIG. 3 illustrates a balloon inflation and deflation timeline relative to various portions of the cardiac cycle in accordance with certain aspects of the present disclosure.

FIG. 3 shows a waveform 202 illustrating a potential sequence of balloon inflations and deflations for the LA balloon 102 against the timing of an ECG signal 200.

In one exemplary implementation of the timing for balloon 102 that can generate the waveforms of FIG. 3, the LA balloon 102 is triggered to deflate upon detection of the R peak plus a time delay (e.g., a 100 millisecond delay after the R peak). In this way, the system initiates deflation of the LA balloon 102 such that deflation of the LA balloon coincides with the natural expansion/reservoir function phase of the LA pressure/volume cycle which occurs during ventricular systole when the mitral valve is closed. LA balloon inflation can be triggered to initiate based on the P wave peak of the ECG or the R peak plus an additional time delay (e.g., a 600 millisecond time delay after the R peak) such that inflation of LA balloon 102 coincides with atrial systole (e.g., with the active contraction portion of the atrial pressure/volume cycle when the a wave peak occurs) at the end of ventricular diastole just before the mitral valve closes to enhance the atrial ventricular pressure differential and increase ventricular filling (e.g., LV End Diastolic Volume, LVEDV).

Figure 4:
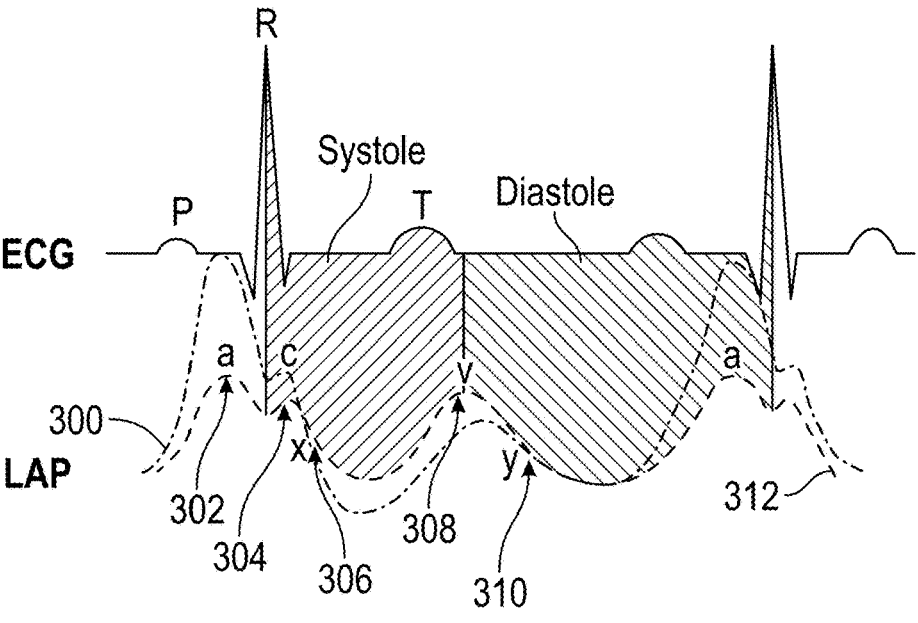
FIG. 4 illustrates the change in left atrial pressure with the use of a left atrial balloon relative to various portions of the cardiac cycle.

FIG. 4 shows two LA pressure waveforms 300, 312 against the timing of an ECG signal. The figure also indicates certain points of the cardiac cycle. For example, the LA contracting 302, the mitral valve closing 304, the LA relaxing and filling 306, the LA is full 308, and the LA emptying 310. The unmodified waveform 312 shows a Left atrial pressure waveform for a heart without the use of a LA balloon and modified waveform 300 shows a Left atrial pressure waveform for a heart with the use of a LA balloon. As shown, the a-wave peak (302 equivalent) of the modified waveform 300 is higher than 302 in the unmodified waveform 312 when the LA contracts due to the inflation of the balloon, this wave boost amplifies the natural contractility of the Left Atrium which may be diminished as a result of atrial dysfunction related to heart failure and/or atrial fibrillation and serves to improve left ventricular filling and support cardiac output. Conversely, the deflation of the balloon just after the R peak causes a lower pressure during the filling of the atrium (306 equivalent) and a lower v-wave peak (308 equivalent) as compared to the unmodified waveform 312. This reduction in filling pressure should result in a decrease in pulmonary capillary wedge pressure and pulmonary congestion.

FIGS. 5-9 show exemplary implementations of LA balloon 102 and atrial positioning structure 106.

In general, balloon 102 can be separate from its associated positioning structure or can be incorporated with a positioning structure. In either implementation, a positioning structure is provided that maintains the position of its associated balloon within the heart throughout the cardiac cycle. In the example perspective views of FIG. 5, LA balloon 102 is a dome-shaped expandable structure that is attached to atrial positioning structure 106 configured to be positioned transseptally with a portion 700 that extends through the atrial septum. Portion 700 can also be considered an atrial positioning structure, and may comprise a catheter body as described above that is temporarily positioned within the heart or a shorter trans-septal shaft that may be positioned in the heart over a longer term. The atrial positioning structure 106 comprises a toroidal structure comprising an expandable wire mesh (for example, self-expanding, shape-set nitinol wire mesh) that may substantially take the form of two discs 800 and 802, shown more particularly in FIG. 6. The system may be deployed from within a sheath that can constrain the diameter of the positioning structure 106 and the dome-shaped expandable structure 102 as it is delivered transseptally. Once the distal end has been advanced into the Left Atrium, the sheath may be retracted (or the balloon catheter and positioning structure may be advanced relative to the sheath) such that the distal disc with the balloon 102 attached is able to expand within the Left Atrium. The system may then be pulled back towards the Right Atrium to seat the proximal surface of the distal disc against the left atrial facing surface of the septal wall. As the sheath retraction continues, the proximal disc is exposed and expanded such that the distal facing surface of the proximal disc seats against the right atrial facing surface of the septal wall to secure the system relative to the septum. The arrows in FIG. 5 illustrate how balloon 102 can be alternatingly inflated and deflated.

Figure 5:
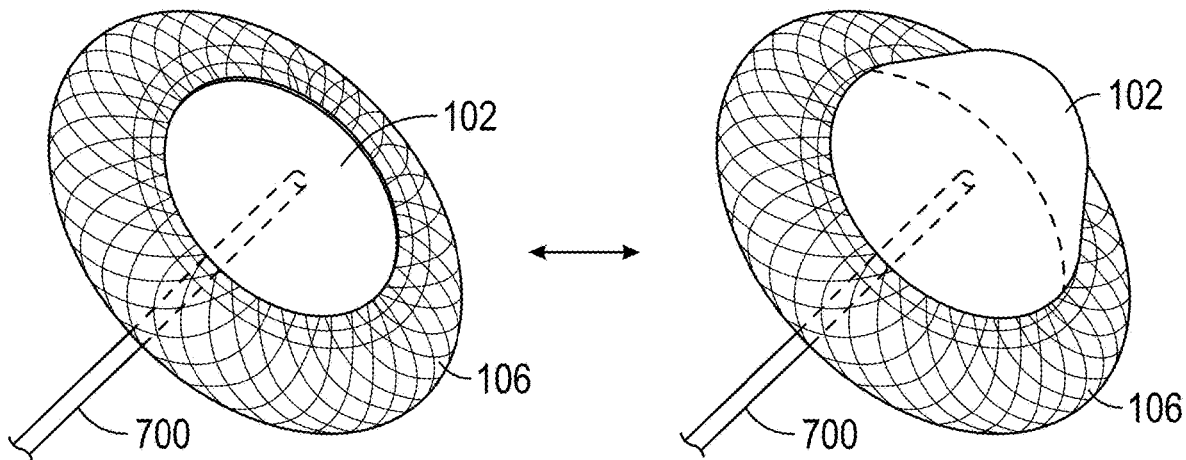
FIG. 5 illustrates perspective views of a left atrial balloon in various states in accordance with various aspects of the subject technology.
Figure 6:
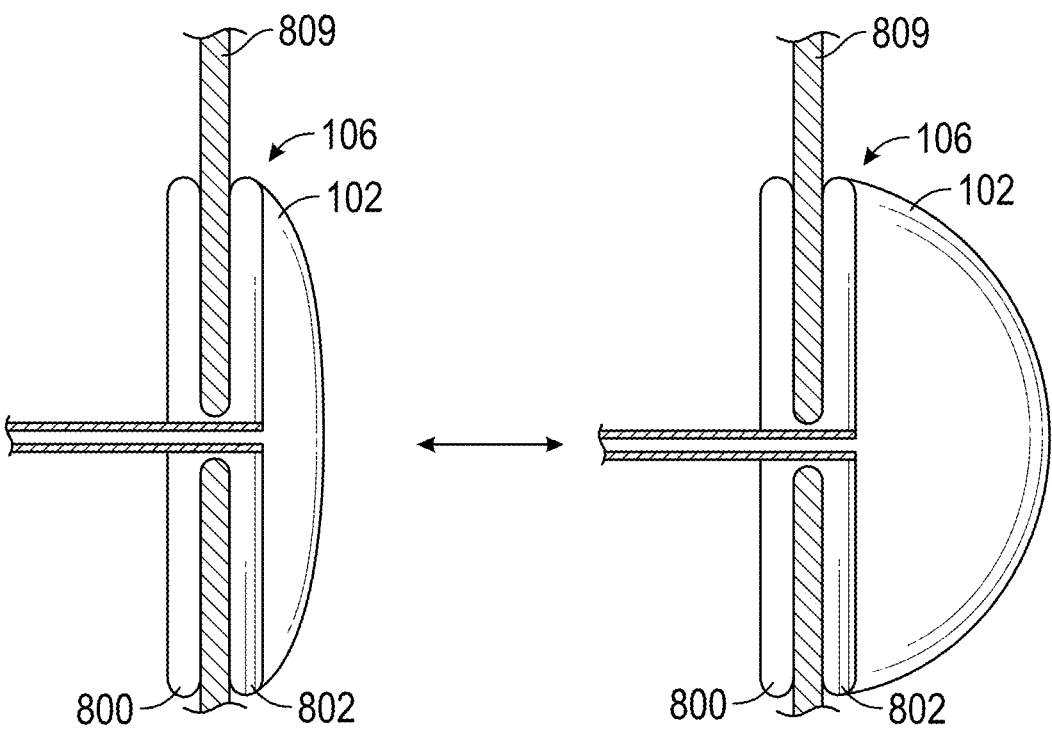
FIG. 6 illustrates partial cross-sectional views of a left atrial balloon in various states in accordance with various aspects of the subject technology.
Figure 7A:
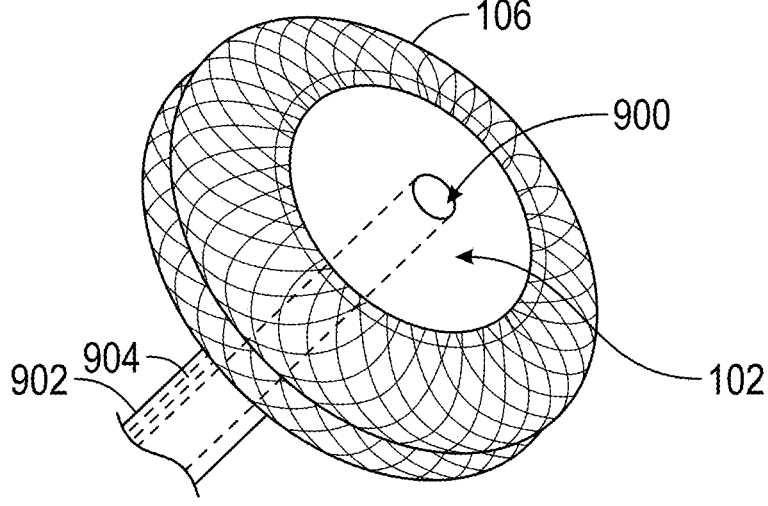
FIG. 7A-7B illustrate a perspective view and a partial cross-sectional view of a left atrial balloon having a trans-septal shaft and a central lumen in accordance with various aspects of the subject technology.
Figure 7B:
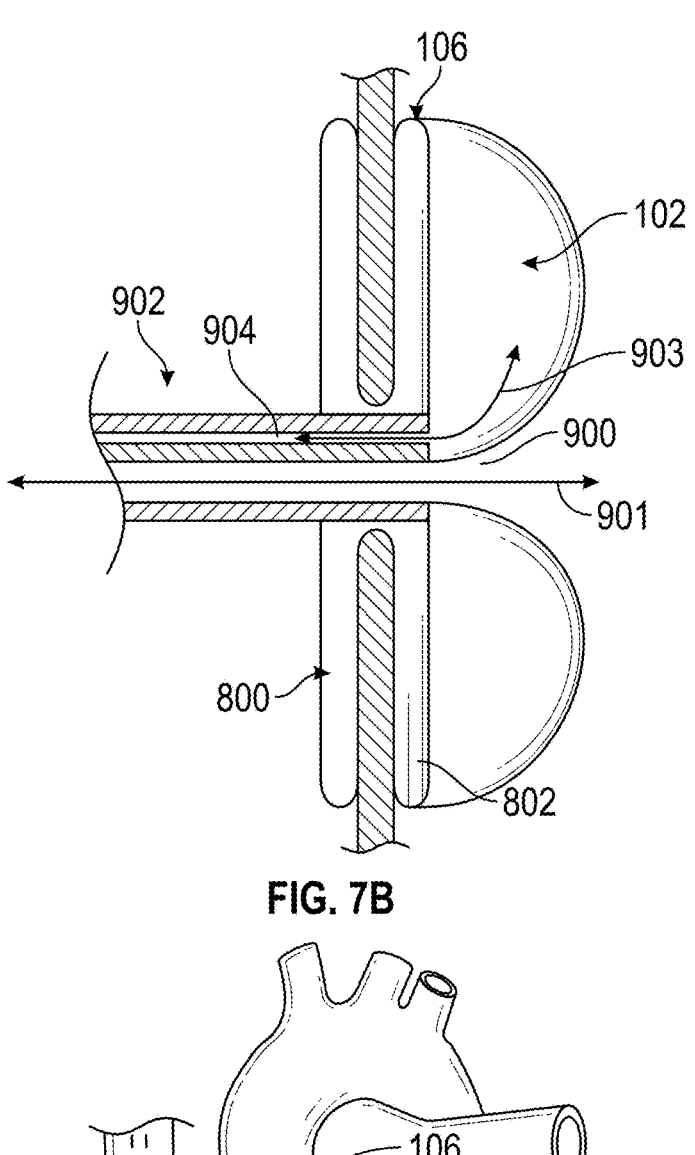

FIG. 6 shows a partial cross-sectional side view of the atrial positioning structure 106 and LA balloon 102 of FIG. 5, anchored with expandable members 800 and 802 on either side of the atrial septum 809 with balloon 102 incorporated into the LA side of the positioning structure 106. Expandable member 800 and 802 can be collapsed for insertion into the patient's heart (and through the atrial septum for member 802) and then expanded to secure positioning structure 106 to the septum. The balloon 102 can comprise anti-thrombotic material. The arrows in FIG. 6 illustrate how balloon 102, once anchored to the septum 809, can be alternatingly inflated and deflated. Although a dome-shaped balloon 106 is shown in FIGS. 6 and 7, it should be appreciated that LA balloon 102 can be shaped as a toroidal loop or other form that allows for trans-septal access to the LA through a central lumen through the balloon 102. The central lumen providing a conduit to the Left Atrium can be used as a guidewire lumen to facilitate initial delivery, direct pressure measurement from a hub on the external portion of the catheter, a pressure sensor (e.g. a fiber optic pressure sensor), a shunt path to the venous system, or any other purpose where access to the Left Atrium may be desired. For example, FIGS. 7A-7B shows an implementation of LA balloon 102 that comprises a multi-lumen catheter 902 that includes an open central lumen 900 for maintaining access to the left atrial chamber. The catheter 902 includes another lumen 904 that can be used to inflate and deflate the balloon 102. A cross-sectional view of FIG. 7A is shown in FIG. 7B. As shown, the central lumen 900 provide access to the left atrial chamber as shown by the double-headed arrow 901. Additionally, the fluid lumen 904 can deliver fluid to and from the balloon 102 as depicted by the second double-headed arrow. 903.

Figure 8:
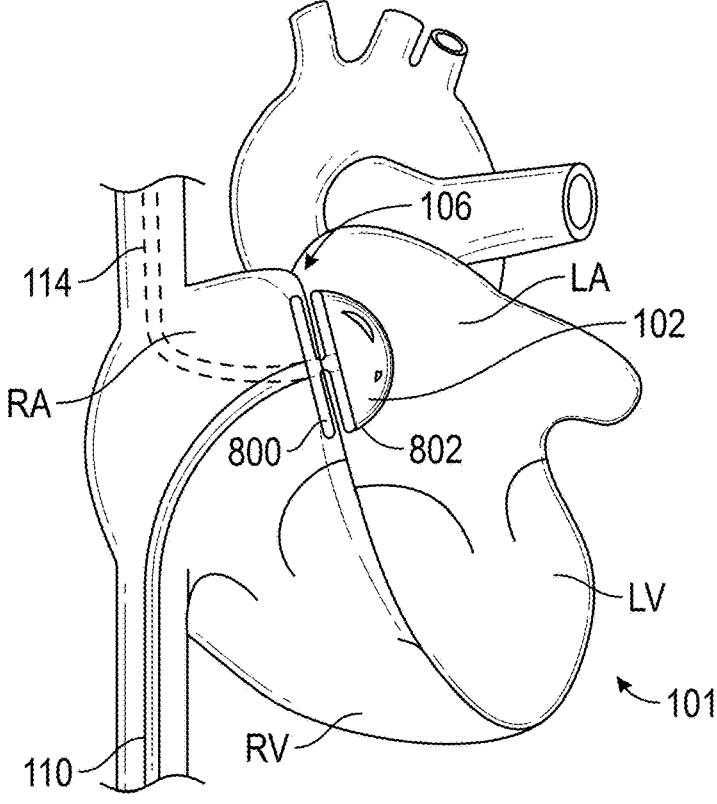
FIG. 8 illustrates an implanted trans-septal left atrial positioning structure and balloon in accordance with various aspects of the subject technology.
Figure 9:
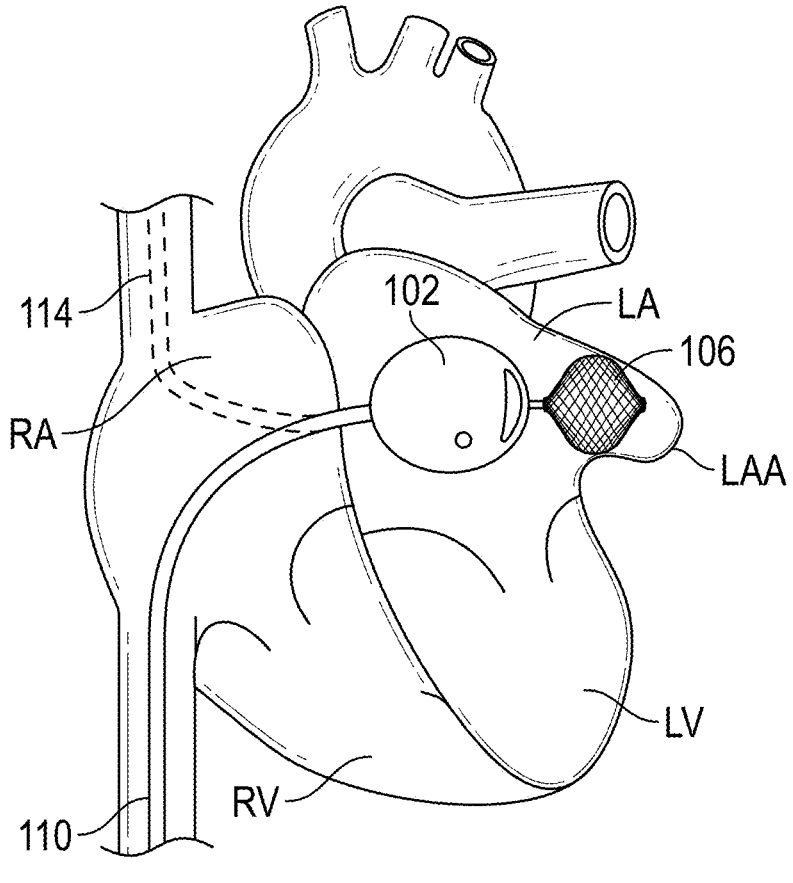
FIG. 9 illustrates an implanted left atrial appendage left atrial positioning structure and balloon in accordance with various aspects of the subject technology.

In some operational scenarios, after temporarily treating the patient for HF, a trans-septal LA balloon and atrial anchoring structure can be removed and the trans-septal opening can be closed or left open. FIG. 8 shows LA balloon 102 positioned in the LA by LA positioning structure 106 implemented as a trans-septal anchor having first and second anchor members 800 and 802 respectively disposed in the right and left atria and LA balloon 102 attached to left-side member 802. FIG. 9 shows an alternate implementation in which LA balloon 102 is anchored with a structure 106 that anchors at a distal end in the left atrial appendage (LAA). Anchoring in the LAA (e.g., with an expandable cage as shown in FIG. 9) can also be implemented such that that structure 106 simultaneously closes off a portion of the LAA in order to help reduce overall LA volume and minimize the risk of embolism and/or the effects of AF. It should also be appreciated that LA anchoring structure 106 can be anchored in other locations to position LA balloon 102 in the LA. In one example, LA anchoring structure 106 may be an anchoring member configured for anchoring in an orifice of one or more pulmonary veins. Additionally, in any of the embodiments described herein, and as indicated in FIGS. 8-9, feed line 110 can access the LA from the superior vena cava (SVC), as illustrated by the dotted line 114, or the inferior vena cava (IVC), as illustrated by the solid line 110, via the right atrium.

Figure 10A:
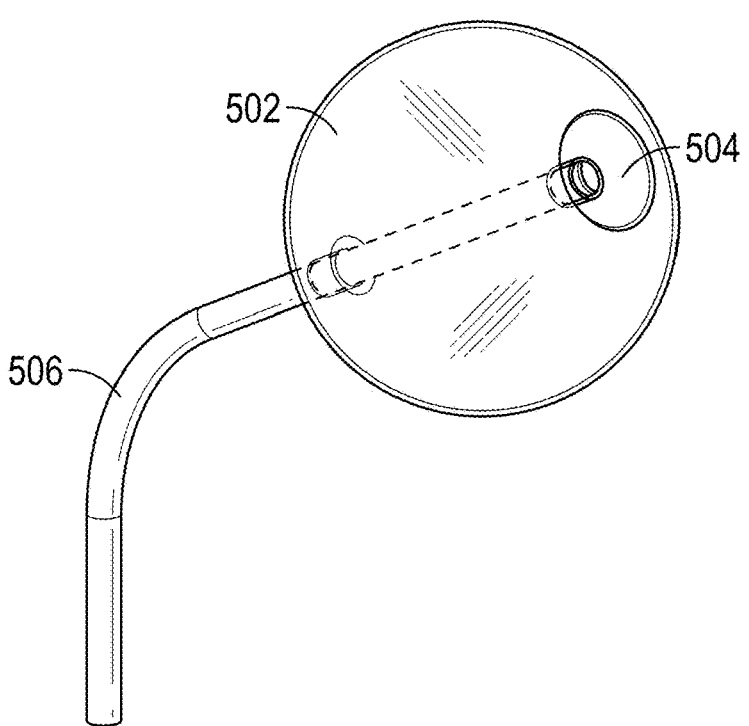
FIGS. 10A-10D illustrate various views of a left atrial balloon in accordance with various aspect of the subject technology.
Figure 10B:
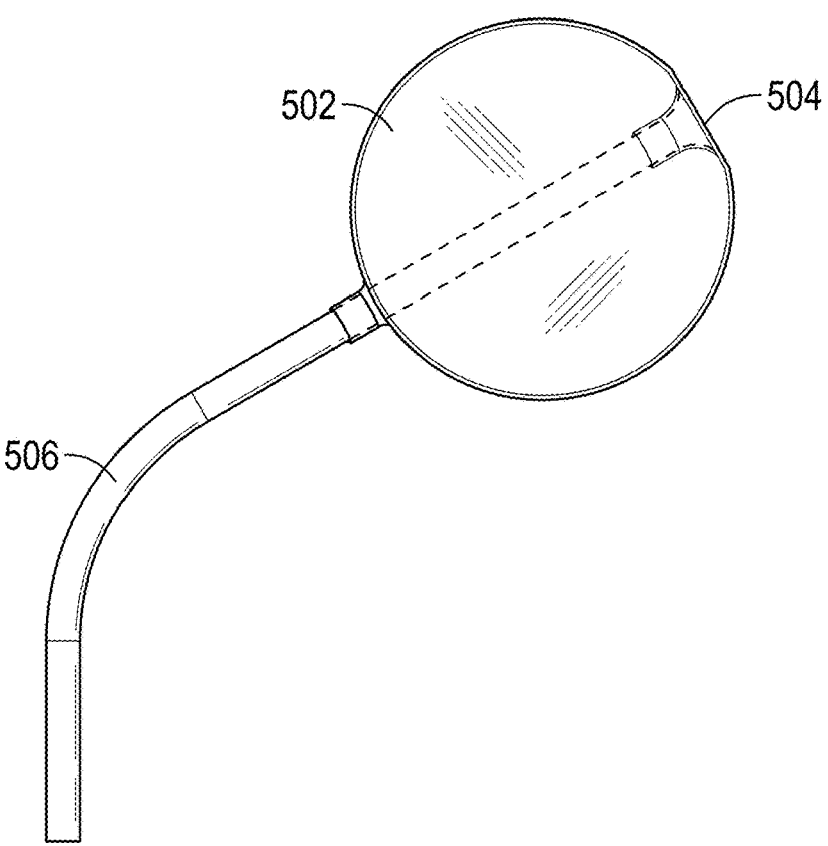
Figure 10C:
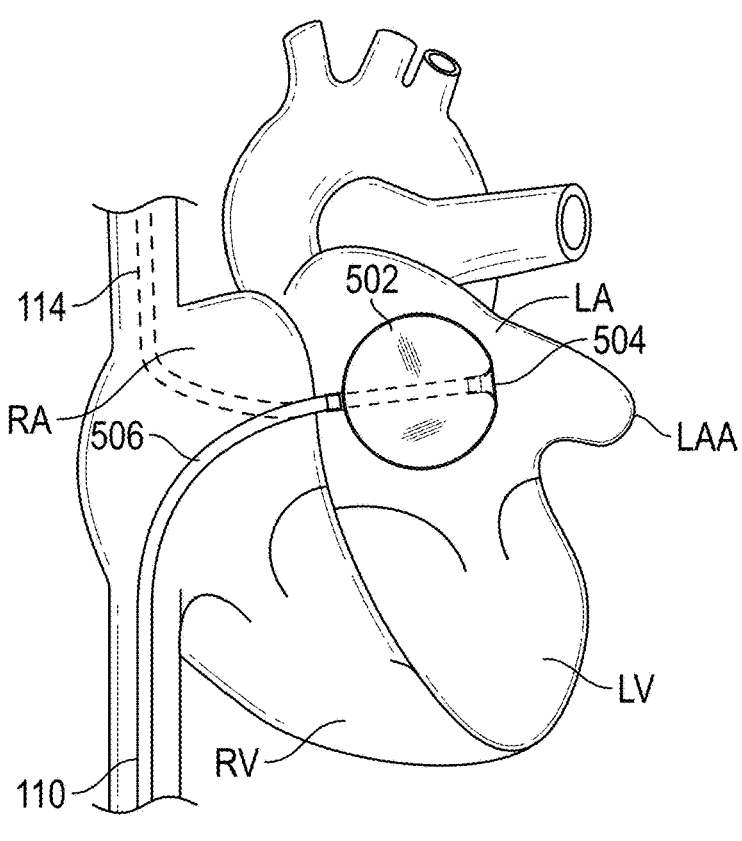
Figure 10D:
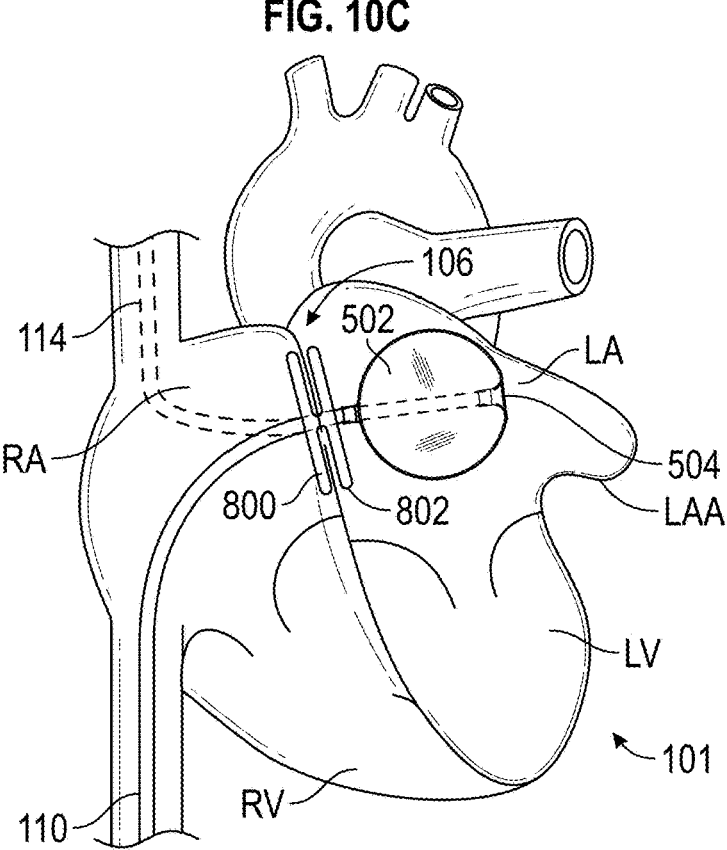

Another implementation of the LA balloon is shown in FIGS. 10A-10D. The distal end 504 of the LA balloon 502 is recessed within the LA balloon 502. The invaginated tip allows for the distal end 504 of the balloon 502 to be atraumatic, including but not limited to instances when a guidewire is not present. The balloon 502 can be anchored to the heart by similar anchoring mechanisms as described above, as shown in FIG. 10D, but it does not require it, as shown in FIG. 10C. FIG. 10C illustrates that the LA balloon 502 can be positioned within the LA using a shaft 506 as the atrial positioning structure. In one implementation, the shaft 506 may be a multi-lumen polymer shaft. The shaft 506 can be pre-formed with a bend or curve of approximately 60 degrees or a variety of different angles to help facilitate proper placement during delivery and stabilization during activation. The shaft 506 can comprise a plurality of lumens. For example, the shaft 506 can have a separate lumen for a guidewire, a separate flow lumen to inflate and deflate the balloon 502, and a separate lumen for a fiber optic pressure sensor. The shaft 506 may also contain a lumen for housing a stiffening stylet for stabilizing the distal tip of the catheter and maintaining balloon position during activation. The stiffening stylet can be inserted before or after the distal tip has been advanced to its desired location. The stiffening stylet may be pre-formed with a bend or curve to impart a desired bend or curve to the shaft 506.

In various implementations, LA balloon 102, 502 can have a shape that is spherical, oval, cylindrical, flat, dome-shaped, toroidal, or any other geometric configuration suitable for pressurizing (e.g., increasing or decreasing pressure in a controllable manner) the LA. The different shapes can improve placement in the patient. In other implementations, the LA balloon 102, 502 can have different sizes to better suit the heart of a patient and/or provide preferential flow patterns upon inflation and/or deflation.

It should also be appreciated that an LA balloon such as LA balloon 102 can be provided in conjunction with one or more other implantable elements.

Figure 11:
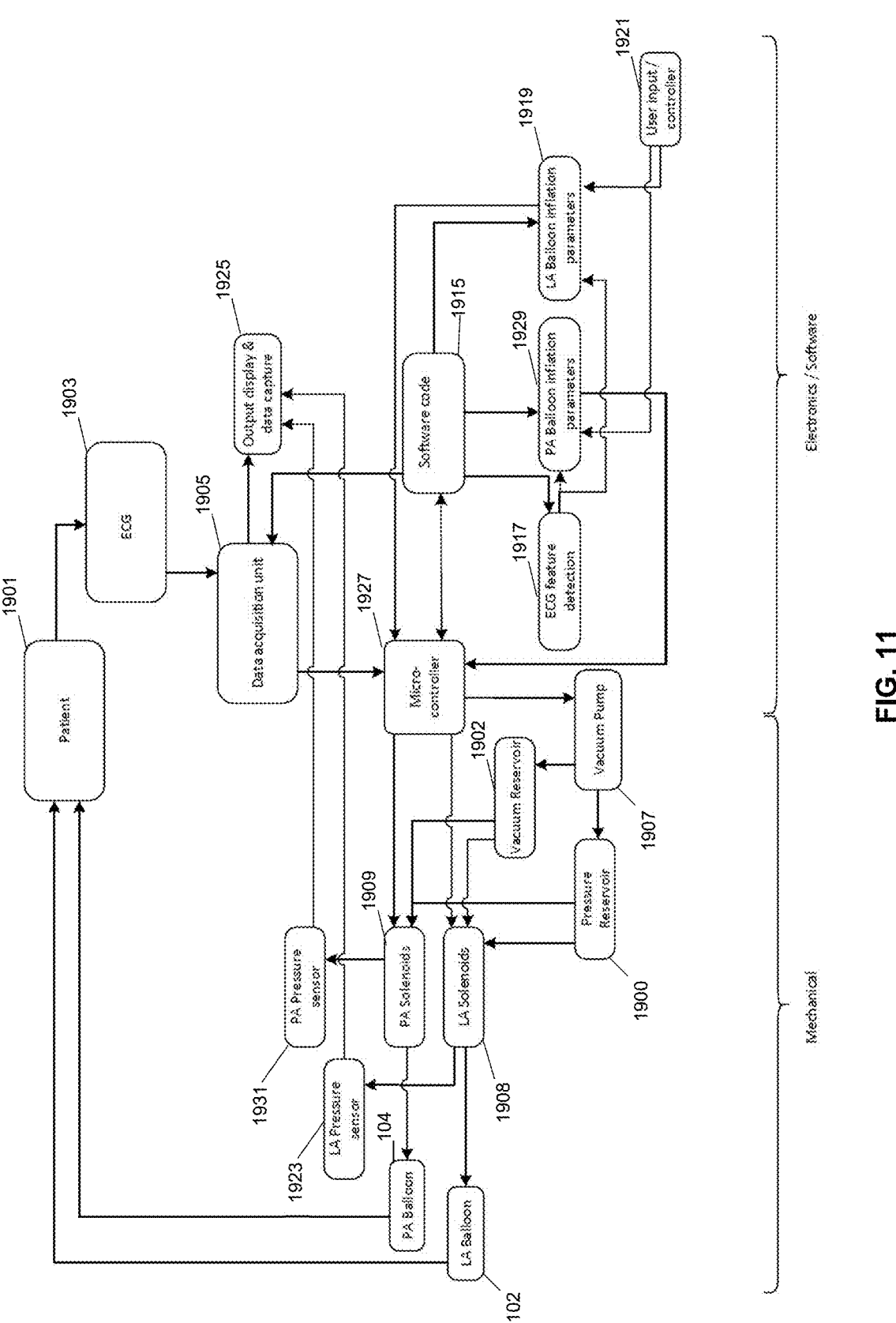
FIG. 11 illustrates a schematic of the components of the systems of FIGS. 2 and 13A-13B in accordance with various aspects of the subject technology.

FIG. 11 shows various components that may be incorporated into system 100 described above that are not visible in FIG. 2 and that are configured to operate LA balloon 102 as described herein. FIG. 11 illustrates components that may be usable in a single balloon system, as described above, or in a dual balloon system, as described further below. Therefore, not all of the components illustrated in FIG. 11 may be needed or utilized for a single balloon system. Further details regarding components of the system 100 are also described in U.S. Provisional Application No. 62/801,819, filed Feb. 6, 2019, including but not limited to FIG. 14 and paragraph [0046], the entirety of which is hereby incorporated by reference. In the example of FIG. 11, system 100 may include control circuitry (not shown), a power source (not shown), a pressure chamber or reservoir 1900, a vacuum chamber or reservoir 1902, and a pump 1907. As shown, solenoids 1908 may be disposed on tubing that fluidly couples pressure chamber 1900 and vacuum chamber 1902 to a fluid line (e.g., implementations of fluid line 110 of FIG. 2) can be controlled by control circuitry at microcontroller 1927 to control the inflation and deflations of balloon 102. In one embodiment, ECG sensors 1903 are connected to the patient 1901 and the patient's ECG signal is sent to the data acquisition unit 1905, which is programmed by the software 1915 to look for a set threshold value that correlates to the R-wave in the ECG signal. Once the threshold is detected, the data acquisition unit 1905 sends a pulse (e.g., square wave) to microcontroller 1927. The software 1915 monitors the microcontroller 1927 for the pulses sent by the data acquisition unit 1905 and uses that information to continuously calculate the interval between R-waves (the R-R interval) of the ECG signal. The LA balloon inflation is timed using the calculated R-R intervals and the parameters 1919 (including length of inflation time, offset/delay time after detection of ECG feature 1917, and fill volume), which may be adjusted with the user input/controller 1921. Based on the R-R interval timing and the user input 1921, the software 1915 then communicates with the microcontroller 1927 to actuate the solenoids 1908, opening the balloon lumen(s) to either the pressure chamber 1900 for inflation, or the vacuum chamber 1902 for deflation.

Although system 100 is depicted as an external fixed system (e.g., for bedside support), the components of FIG. 11 and the other figures described above can also be arranged for ambulatory use, or for implantation in the patient (e.g., the drive system for balloon 102 can be in an external console, a wearable external portable unit, or could be fully implantable). System 100 can be provided for temporary, short-term, mid-term, long-term, or permanent use. In temporary cases, LA positioning structure 106 is arranged to be removed from the patient atraumatically.

If desired, balloon 102 can be provided with a pressure sensor/monitor 1923 that collects pressure data within the corresponding cavity, for example a fiber optic pressure sensor or other similar method. Pressure data from this pressure sensor can be used to drive or trigger the balloon inflation and/or deflation and/or can be collected to provide information to the patient, physician, or others in real-time via an output display 1925 or when uploaded separately. In some embodiments, sensors 1923 may also be used to monitor pressure inside the balloon for various purposes.

Although various examples are discussed herein in which LA pressurizing element 102 is implemented as a balloon, it should be appreciated that LA support system 100 can be implemented with other pressurizing elements such as active pumps, axial flow pumps, turbines, or other mechanisms for displacing volume and fluids. More generally, element 102 can be implemented as any suitable combination of pressurizing (e.g., pressure-control), fluid-displacement, and/or volume-displacement mechanisms that are biocompatible and implantable for positioning in fluid communication with one or more portions of the left side of a patient's heart. For example, LA pressurizing element 102, when operated, may cause a volume displacement in the Left Atrium.

Figure 12:
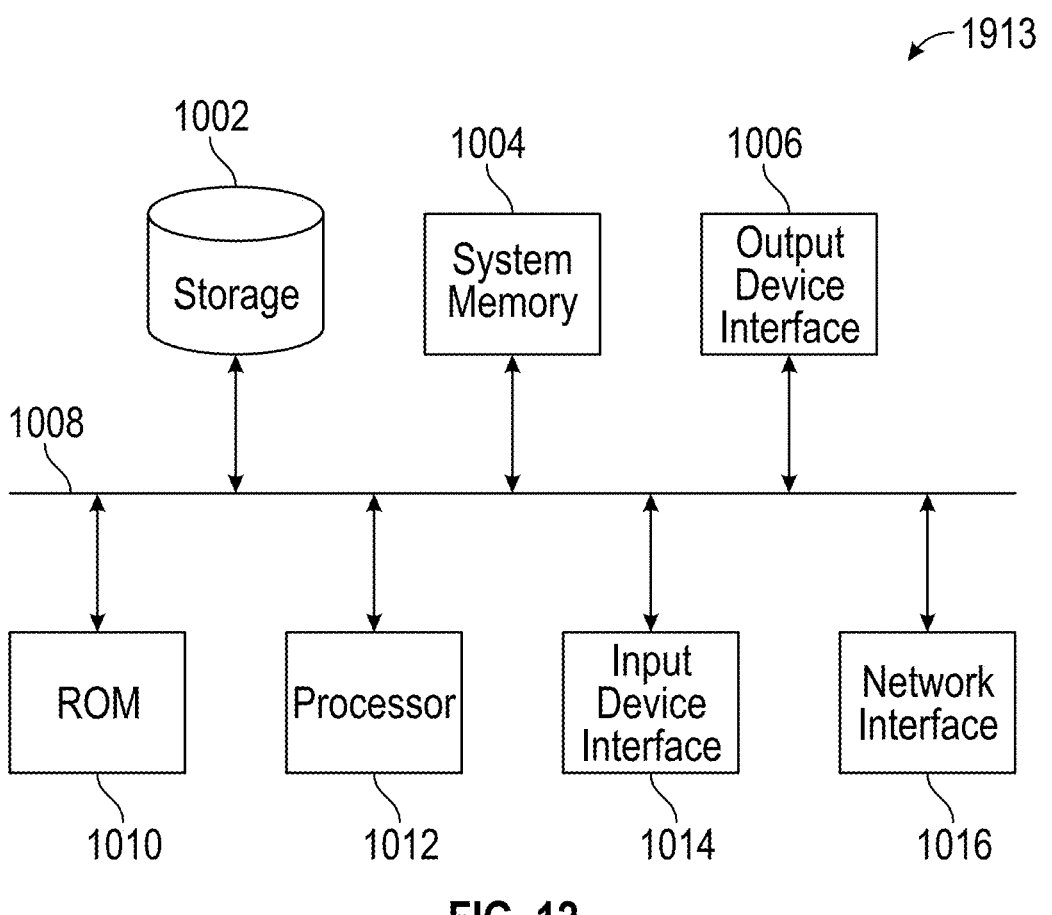
FIG. 12 illustrates a system with which one or more implementations of the subject technology may be implemented.

FIG. 12 conceptually illustrates an electronic system with which one or more aspects of the subject technology may be implemented. Electronic system, for example, may be, or may be a part of, control circuitry 1913 for a left atrial support system implemented in standalone device, a portable electronic device such as a laptop computer, a tablet computer, a phone, a wearable device, or a personal digital assistant (PDA), or generally any electronic device that can be communicatively coupled to pressurizing devices implanted in a patient's heart and or pulmonary vasculature. Such an electronic system includes various types of computer readable media and interfaces for various other types of computer readable media. Electronic system includes bus 1008, processing unit(s) 1012, system memory 1004, read-only memory (ROM) 1010, permanent storage device 1002, input device interface 1014, output device interface 1006, and network interface 1016, or subsets and variations thereof.

Bus 1008 collectively represents all system, peripheral, and chipset buses that communicatively connect the numerous internal devices of electronic system. In one or more embodiments, bus 1008 communicatively connects processing unit(s) 1012 with ROM 1010, system memory 1004, and permanent storage device 1002. From these various memory units, processing unit(s) 1012 retrieves instructions to execute and data to process in order to execute the processes of the subject disclosure. The processing unit(s) can be a single processor or a multi-core processor in different embodiments.

ROM 1010 stores static data and instructions that are needed by processing unit(s) 1012 and other modules of the electronic system. Permanent storage device 1002, on the other hand, is a read-and-write memory device. This device is a non-volatile memory unit that stores instructions and data even when electronic system is off. One or more embodiments of the subject disclosure use a mass-storage device (such as a magnetic or optical disk and its corresponding disk drive) as permanent storage device 1002.

Other embodiments use a removable storage device (such as a floppy disk, flash drive, and its corresponding disk drive) as permanent storage device 1002. Like permanent storage device 1002, system memory 1004 is a read-and-write memory device. However, unlike storage device 1002, system memory 1004 is a volatile read-and-write memory, such as random access memory. System memory 1004 stores any of the instructions and data that processing unit(s) 1012 needs at runtime. In one or more embodiments, the processes of the subject disclosure are stored in system memory 1004, permanent storage device 1002, and/or ROM 1010. From these various memory units, processing unit(s) 1012 retrieves instructions to execute and data to process in order to execute the processes of one or more embodiments.

Bus 1008 also connects to input and output device interfaces 1014 and 1006. Input device interface 1014 enables a user to communicate information and select commands to the electronic system and/or a sensor to communicate sensor data to processor 1012. Input devices used with input device interface 1014 include, for example, alphanumeric keyboards, pointing devices (also called "cursor control devices"), cameras or other imaging sensors, electro-cardio sensors, pressure sensors, or generally any device that can receive input. Output device interface 1006 enables, for example, the display of images generated by electronic system. Output devices used with output device interface 1006 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more embodiments may include devices that function as both input and output devices, such as a touch screen. In these embodiments, feedback provided to the user can be any form of sensory feedback, such as visual feedback, auditory feedback, or tactile feedback; and input from the user can be received in any form, including acoustic, speech, or tactile input. Output device interface 1006 may also be used to output control commands for operating pressurizing components (e.g., to control pressurizing element 102) as described herein.

Finally, as shown in FIG. 12, bus 1008 also couples electronic system to a network (not shown) through network interface 1016. In this manner, the computer can be a part of a network of computers (such as a local area network ("LAN"), a wide area network ("WAN"), or an Intranet, or a network of networks, such as the Internet. Any or all components of electronic system can be used in conjunction with the subject disclosure.

Dual Cardiac Support System

Figure 13A:
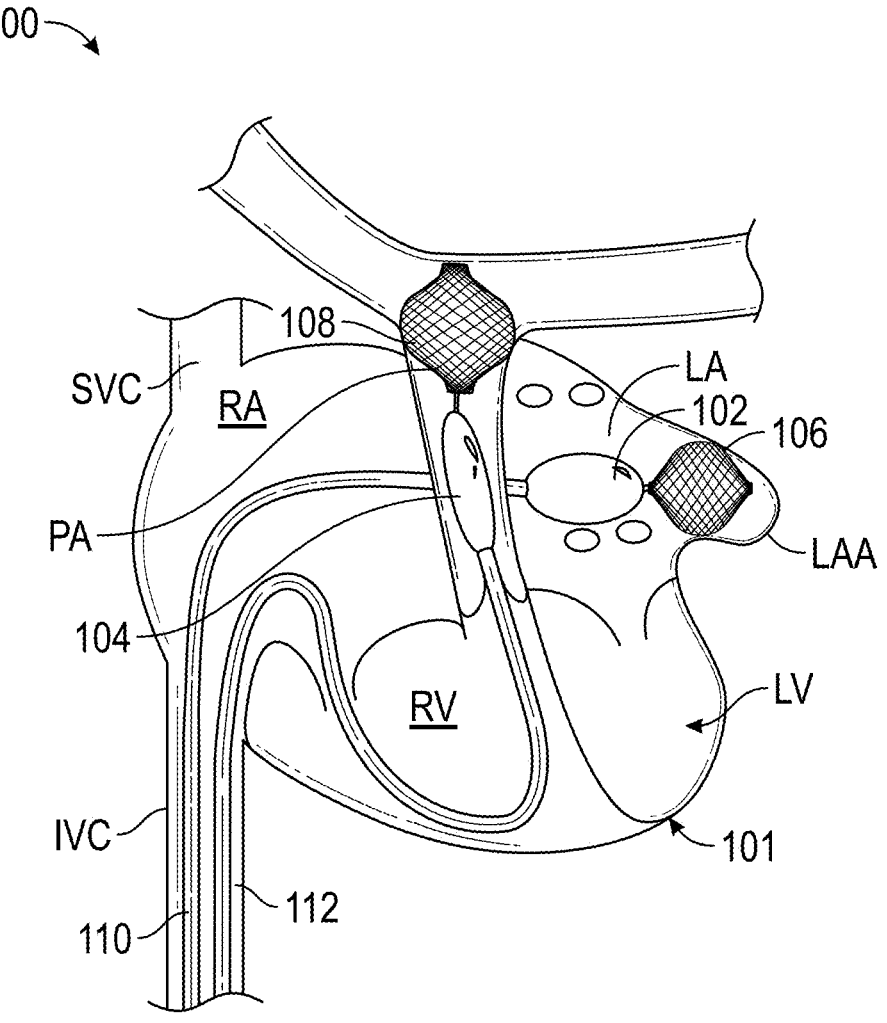
FIGS. 13A-13B illustrates a dual-sided cardiac support system in inflated and deflated states according to certain aspects of the present disclosure.
Figure 13B:
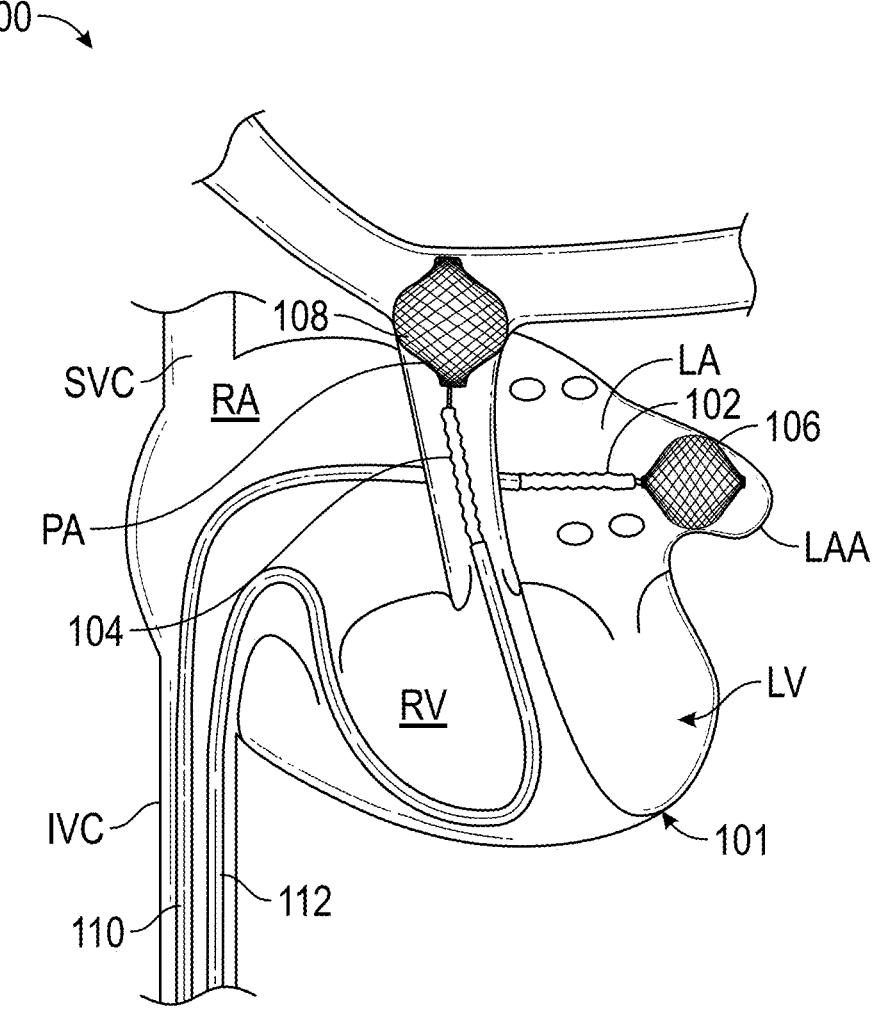

FIGS. 13A-13B illustrate another example system 600 in which two implantable pressurizing elements have been implanted in the patient. In the example of FIGS. 13A-13B, system 600 includes a first pressurizing element 102 implemented as a balloon for illustrative purposes. As shown, an atrial positioning structure 106 is coupled to the first pressurizing element 102 and configured to position the first pressurizing element 102 in a Left Atrium LA of a heart 101 of a patient. Any of the atrial positioning structures described above may be utilized in the system 600 as described herein. As shown, system 600 also includes a second pressurizing element 104 and a pulmonary artery positioning structure 108 coupled to the second pressurizing element 104 and configured to position the second pressurizing element 104 in a Pulmonary Artery PA of the patient. Although not visible in FIGS. 13A-13B, system 600 also includes control circuitry configured to operate the first and second pressurizing elements 102, 104 to generate coordinated pressure modifications and/or volume displacements in the Left Atrium and the Pulmonary Artery. Feed lines 110 and 112 are shown, through which a fluid or a gas can be provided or removed for inflation or deflation of balloon implementations of pressurizing elements 102 and 104, or with which control signals can be provided for operation of other implementations of pressurizing elements 102 and 104. As described above, the feed line 110 may be incorporated into or be part of an elongate catheter body used to deliver the pressurizing element 102 to the Left Atrium LA. The feed line 112 may be incorporated into or be part of an elongate catheter used to deliver the pressurizing element 104 and the pulmonary artery positioning structure 108 to the right side of the heart. For example, in both balloon and non-balloon embodiments, in some aspects a catheter or sheath may be delivered in a percutaneous approach through the femoral vein and advanced through the inferior vena cava, to the Right Atrium RA, to the Right Ventricle RV, and into the Pulmonary Artery PA. The pressurizing element 104 is positioned at or near a distal end of the elongate body and may be expanded in the PA. An expandable pulmonary artery positioning structure 108, shown distal to the balloon in FIGS. 13A and 13B, may expand in the Pulmonary Artery (or elsewhere) to help secure the balloon within the PA. In some embodiments, the pulmonary artery positioning structure 108 comprises an expandable cage that may be secured at the bifurcation of the PA.

System 600 may also include one or more sensors such as electrocardiogram (ECG) sensors and/or pressure sensors that generate signals that correspond to portions of the cardiac cycle of the patient. Pressurizing elements 102 and 104 can be operated to generate coordinated pressure changes (e.g., pressure increases and/or pressure decreases) in the Left Atrium and Pulmonary Artery respectively, in coordination with various portions of the cardiac cycle based on the signals from the sensor.

In accordance with aspects of the present disclosure, the dual-sided system 600 of FIGS. 13A-13B is provided to address potential dysfunction on both sides of the heart. In contrast with HFpEF treatments with devices that merely reduce LA pressure only at the cost of increasing the burden on the right side of the heart and reducing cardiac output, system 600 as described herein supports the heart by unloading the burden on both side of the lungs, thereby reducing congestion and pulmonary wedge pressure and improving LV diastolic filling to support cardiac output. This is achieved by placing one fluid/volume displacing system on the left side of the heart (e.g., pressurizing element 102 in the Left Atrium) and another fluid/volume displacing system on the right side of the heart (e.g., pressurizing element 104 in the Pulmonary Artery). In the example discussed herein in which pressurizing element 102 and pressurizing element 104 are implemented as balloons, the coordinated inflation (see FIG. 13A) and deflation of the balloons (see FIG. 13B) is timed in such a way to optimize support for each patient and keep blood moving in the proper direction at all times during the cardiac cycle. FIG. 13A illustrates when the balloons 102, 104 are inflated and FIG. 13B illustrates when the balloons 102, 104 are deflated.

On the right side, deflation of the balloon can serve to reduce the afterload and work required of the Right Ventricle and improve filling efficiency in the lungs during inflation, as shown in FIG. 13B. For example, actively deflating the PA balloon 104 during PA systole will reduce PA systolic pressures and RV work load. Then subsequently inflating the PA balloon 104, as shown in FIG. 13A, during PA diastole after the pulmonary valve is closed will increase PA diastolic pressure and help overcome pulmonary vascular resistance to provide greater cardiac output. On the left side, deflation of a balloon 102 in the Left Atrium during atrial diastole can help draw oxygenated blood out of the lungs by simulating an increase in LA reservoir strain (e.g., increase in volume during filling) increasing the relative volume of the LA and reducing the filling pressures. Then, by inflating balloon 102 during the active portion of the diastolic cycle (e.g., during atrial systole) the balloon can simulate an increase in LA pump/active strain by reducing the relative volume in the LA and increasing LA pressure during the active phase of the cycle, thereby increasing the LA-to-LV pressure differential and improving diastolic filling of the Left Ventricle. This coordinated operation of LA balloon 102 and PA balloon 104 serves to restore compliance to areas of the heart (e.g., the LA and PA) that are experiencing increased stiffness and wall stress.

In various operational scenarios, balloons 102 and 104 (or other implementations of the pressurizing elements for fluid/volume displacement in the LA and PA) can be operated independently or in concert (e.g., with direct synchronicity, exact opposite functionality, or an overlapping sequence with different delays in timing of inflation and deflation throughout the cardiac cycle), depending on the placement of the balloons and the specific needs of each patient.

Inflation and deflation of balloons 102 and 104 can be based on an initial (e.g., fixed) timing or can be triggered by sensor signals from electrocardiogram (e.g., EKG or ECG)

sensors, pressure sensors (e.g., a pressure sensor in or near the LA and a pressure sensor in our near the PA), or a combination thereof.

As described above, FIG. 3 shows a waveform 202 illustrating a potential sequence of balloon inflations and deflations for the LA balloon 102 against the timing of an ECG signal 200. FIG. 3 also shows a waveform 204 illustrating a potential sequence of balloon inflations and deflations for the PA balloon 104.

In one exemplary implementation of the timing for balloons 102 and 104 that can generate the waveforms of FIG. 3, the PA balloon 104 is triggered to deflate upon detection of the R peak in the ECG signal and inflate upon detection of the T peak in the ECG signal (or a specific timing offset from the R peak that coincides with the T wave) so that the deflation and inflation coincide with the opening and closing of the pulmonary valve, respectively—and the beginning of systole and diastole respectively. In this example, the LA balloon 102 is triggered to deflate upon detection of the R peak plus a time delay (e.g., a 100 millisecond delay after the R peak). In this way, the system initiates deflation of LA balloon 102 right after initiating the deflation of the PA balloon 104 such that deflation of the LA balloon 102 coincides with the natural expansion/reservoir function phase of the LA pressure/volume cycle which occurs during ventricular systole when the mitral valve is closed. LA balloon 102 inflation can be triggered to initiate based on detection of the peak of the P wave of the ECG or the R peak plus an additional time delay (e.g., a 600 millisecond time delay after the R peak) such that inflation of LA balloon 102 coincides with atrial systole (e.g., with the active contraction portion of the atrial pressure/volume cycle when the a-wave peak occurs) at the end of ventricular diastole just before the mitral valve closes to enhance the atrial ventricular pressure differential and increase ventricular filling (e.g., LV End Diastolic Volume, LVEDV).

FIG. 7 of U.S. Provisional Application No. 62/801,917, filed Feb. 6, 2019, the entirety of which is incorporated by reference herein, shows a series of wave forms that indicate Aortic, PA, Atrial, and Ventricular pressure over the course of two cardiac cycles, against the timing of an ECG signal 1604. In addition, a waveform 1600 illustrating a potential sequence of balloon inflations and deflations for the LA balloon 102 and a waveform 1602 illustrating a potential sequence of balloon inflations and deflations for PA balloon 104 are also shown. In addition, the resulting impact of the balloon inflations of waveforms 1600 and 1602 on the LA and PA pressure waves are illustrated in augmented LA pressure waveform 1606 and augmented PA pressure waveform 1608.

As illustrated in FIGS. 14-17, for PA balloon 104, the PA positioning structure 108 can be distal to the balloon 104 and can be implemented as an expandable cage that anchors against the walls of the PA after expansion from an elongated configuration as shown in FIG. 14 (e.g., for passing through the vascular system to the PA) through an intermediately expanded configuration as shown in FIG. 15, to a fully expanded configuration as shown in FIG. 16 (e.g., rotating a coupled torque shaft counterclockwise could extend the proximal portion from the distal portion along an internal thread and compress the anchoring structure, while rotating the torque shaft clockwise could bring the distal and proximal ends of the anchoring structure closer together and expand its diameter). FIG. 16 also shows PA balloon 104 in an inflated configuration. Also shown in FIGS. 14-16 is a guidewire 120 that can be independently inserted and advanced into the desired location within the anatomy (in this case the PA) before the balloon catheter and anchoring system are introduced, such that the balloon catheter and anchoring system can be tracked into position over the guidewire. The guidewire can then be removed or left in place during the course of treatment.

Although FIGS. 14-17 show PA positioning structure 108 distally disposed relative to PA balloon 104, it should be appreciated that PA positioning structure 108 can be disposed proximal to PA balloon 104 or incorporated in-line with the balloon (e.g., as a cage around the balloon). As indicated in FIG. 16, PA positioning structure 108 allows blood flow therethrough.

FIG. 17 shows PA balloon 104 positioned within the PA by PA positioning structure 108 implemented as an expanded cage at the top of the PA. As indicated in FIG. 17, feed line 112 can access the PA from the SVC or inferior IVC, as illustrated by the solid line 112, via the right atrium and right ventricle.

In various implementations, LA balloon 102 and PA balloon 104 can have the same shape or different shapes, with the shape of either balloon being spherical, oval, cylindrical, flat, dome-shaped, toroidal, or any other geometric configuration suitable for pressurizing (e.g., increasing or decreasing pressure in a controllable manner) the LA and/or the PA.

Figure 18:
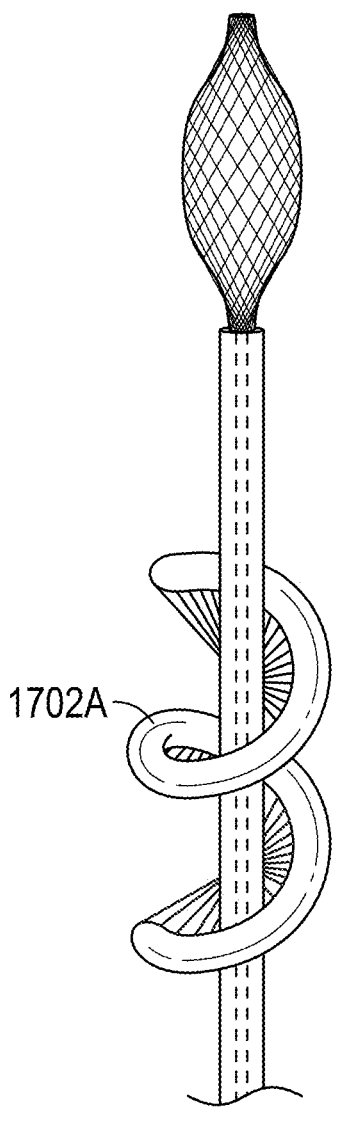
FIG. 18 illustrates a system having a spiral-shaped right ventricle balloon in accordance with various aspects of the subject technology.

Although HFpEF treatments using a system 100 having a LA pressurizing element 102 and a PA pressurizing element 104 are described herein, other systems for treatment of HFpEF and/or AF are contemplated herein that address the dual-sided problem in accordance with the cardiac cycle features discussed in connection with FIG. 2. As another example, FIG. 18 illustrates a balloon 1702A that is shaped as a spiral to enhance forward flow boost. The balloon 1702A may be configured for positioning in the PA as described above. In other embodiments, any of the balloons or pressurizing elements as described herein in the PA may be configured for positioning in the Right Ventricle RV.

FIG. 11 shows various components that may be incorporated into system 600 described above that are not visible in FIGS. 13A-13B and that are configured to operate LA balloon 102 and PA balloon 104 as described herein. Further details regarding components of the system 100 are also described in U.S. Provisional Application No. 62/801,917, filed Feb. 6, 2019, including but not limited to FIG. 21 and paragraph [0057], the entirety of which is hereby incorporated by reference. In the example of FIG. 11, system 600 may include control circuitry (not shown), a power source (not shown), a pressure chamber or reservoir 1900, a vacuum chamber or reservoir 1902, and a pump 1907. As shown, solenoids 1908, 1909 may be disposed on tubing that fluidly couples pressure chamber 1900 and vacuum chamber 1902 to fluid lines (e.g., implementations of fluid lines 110 and 112 of FIGS. 13A-13B) can be controlled by control circuitry at microprocessor 1927 to control the inflation and deflations of balloons 102 and 104. In one embodiment, ECG sensors 1903 are connected to the patient 1901 and the patient's ECG signal is sent to the data acquisition unit 1905 (Power Lab), which is programmed to look for a set threshold value that correlates to the R-wave in the ECG signal. Once the threshold is detected, the data acquisition unit 1905 sends a pulse (square wave) to a microcontroller 1927. The software 1915 monitors the microcontroller 1927 for the pulses sent by the data acquisition unit 1905 and uses that information to continuously calculate the interval between R-waves (the R-R interval) of the ECG signal. The PA and LA balloon inflation is timed using the calculated R-R intervals and the parameters 1919, 1929 (including length of inflation time, offset/delay time after detection of ECG feature 1917, and fill volume), which are adjusted with the user input/controller 1921. Based on the R-R interval timing and the user input 1921, the software then communicates with the microcontroller 1927 to actuate the solenoids 1908, 1909, opening the balloon lumen(s) to either the pressure chamber 1900 for inflation, or the vacuum chamber 1902 for deflation.

Although system 600 is depicted as an external fixed system (e.g., for bedside support), the components of FIG. 11 and the other figures described above can also be arranged for ambulatory use, or for implantation in the patient (e.g., the drive system for balloons 102 and 104 can be in an external console, a wearable external portable unit, or could be fully implantable). System 600 can provided for temporary, short-term, mid-term, long-term, or permanent use. In temporary cases, LA and PA positioning structures 106 and 108 are arranged to be removed from the patient atraumatically.

If desired, balloons 102 and/or 104 can be provided with a pressure sensor/monitor 1923, 1931 that collect pressure data within the corresponding cavity. Pressure data from these pressure sensors can be used to drive or trigger the balloon inflation and/or deflation and/or can be collected to provide information to the patient, physician, or others in real-time via an output display 1925 or when uploaded separately. In some embodiments, sensors 1923, 1931 may also be used to monitor pressure inside the balloons for various purposes.

Although various examples are discussed herein in which LA pressurizing element 102 and PA pressurizing element 104 are implemented as balloons, it should be appreciated that dual-sided system 600 can be implemented with other pressurizing elements such as active pumps, axial flow pumps, turbines, or other mechanisms for displacing volume and fluids. More generally, each of elements 102 and 104 can be implemented as any suitable combination of pressure-control, fluid-displacement, and/or volume-displacement mechanisms that are biocompatible and implantable for positioning in fluid communication with one or more portions of the left or right side of a patient's heart. For example, LA pressurizing element 102, when operated, may cause a volume displacement in the Left Atrium, and PA pressurizing element 104, when operated, may cause a volume displacement in the Pulmonary Artery. As would be understood by one of ordinary skill in the art, the left side of the heart includes the Left Atrium and the Left Ventricle, and receives oxygen-rich blood from the lungs and pumps the oxygen-rich blood to the body. As would be understood by one of ordinary skill in the art, the right side of the heart includes the right atrium and the right ventricle, and receives blood from the body and pumps the blood to the lungs for oxygenation.

Similar to the single balloon system described above, FIG. 12 conceptually illustrates an electronic system with which one or more aspects of the subject technology may be implemented. Electronic system, for example, may be, or may be a part of, control circuitry 1913 for a dual-sided cardio-pulmonary support system implemented in stand-alone device, a portable electronic device such as a laptop computer, a tablet computer, a phone, a wearable device, or a personal digital assistant (PDA), or generally any electronic device that can be communicatively coupled to pressurizing devices implanted in a patient's heart and or pulmonary vasculature. Such an electronic system includes various types of computer readable media and interfaces for various other types of computer readable media. Electronic system includes bus 1008, processing unit(s) 1012, system memory 1004, read-only memory (ROM) 1010, permanent storage device 1002, input device interface 1014, output device interface 1006, and network interface 1016, or subsets and variations thereof.

Bus 1008 collectively represents all system, peripheral, and chipset buses that communicatively connect the numerous internal devices of electronic system. In one or more embodiments, bus 1008 communicatively connects processing unit(s) 1012 with ROM 1010, system memory 1004, and permanent storage device 1002. From these various memory units, processing unit(s) 1012 retrieves instructions to execute and data to process in order to execute the processes of the subject disclosure. The processing unit(s) can be a single processor or a multi-core processor in different embodiments.

ROM 1010 stores static data and instructions that are needed by processing unit(s) 1012 and other modules of the electronic system. Permanent storage device 1002, on the other hand, is a read-and-write memory device. This device is a non-volatile memory unit that stores instructions and data even when electronic system is off. One or more embodiments of the subject disclosure use a mass-storage device (such as a magnetic or optical disk and its corresponding disk drive) as permanent storage device 1002).

Other embodiments use a removable storage device (such as a floppy disk, flash drive, and its corresponding disk drive) as permanent storage device 1002. Like permanent storage device 1002, system memory 1004 is a read-and-write memory device. However, unlike storage device 1002, system memory 1004 is a volatile read-and-write memory, such as random access memory. System memory 1004 stores any of the instructions and data that processing unit(s) 1012 needs at runtime. In one or more embodiments, the processes of the subject disclosure are stored in system memory 1004, permanent storage device 1002, and/or ROM 1010. From these various memory units, processing unit(s) 1012 retrieves instructions to execute and data to process in order to execute the processes of one or more embodiments.

Bus 1008 also connects to input and output device interfaces 1014 and 1006. Input device interface 1014 enables a user to communicate information and select commands to the electronic system and/or a sensor to communicate sensor data to processor 1012. Input devices used with input device interface 1014 include, for example, alphanumeric keyboards, pointing devices (also called "cursor control devices"), cameras or other imaging sensors, electro-cardio sensors, pressure sensors, or generally any device that can receive input. Output device interface 1006 enables, for example, the display of images generated by electronic system. Output devices used with output device interface 1006 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more embodiments may include devices that function as both input and output devices, such as a touch screen. In these embodiments, feedback provided to the user can be any form of sensory feedback, such as visual feedback, auditory feedback, or tactile feedback; and input from the user can be received in any form, including acoustic, speech, or tactile input. Output device interface 1006 may also be used to output control commands for operating pressurizing components (e.g., to control pressurizing elements 102 and 104) as described herein.

Finally, as shown in FIG. 12, bus 1008 also couples electronic system to a network (not shown) through network interface 1016. In this manner, the computer can be a part of a network of computers (such as a local area network ("LAN"), a wide area network ("WAN"), or an Intranet, or a network of networks, such as the Internet. Any or all components of electronic system can be used in conjunction with the subject disclosure.

Other Variations and Terminology

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra-density optical discs, any other optical or magnetic media, and floppy disks. In one or more embodiments, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more embodiments, the computer readable media is non-transitory computer readable media, computer readable storage media, or non-transitory computer readable storage media.

In one or more embodiments, a computer program product (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more embodiments are performed by one or more integrated circuits, such as application specific integrated circuits (ASICs) or field programmable gate arrays (FPGAs). In one or more embodiments, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon implementation preferences, it is understood that the specific order or hierarchy of blocks in the processes may be rearranged, or that not all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The subject technology is illustrated, for example, according to various aspects described above. The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that some or all steps, operations, or processes may be performed automatically, without the intervention of a user. Method claims may be provided to present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the appended claims. Moreover, nothing disclosed herein is intended to be dedicated to the public regardless of whether such disclosure is explicitly recited in the claims. No claims element is to be construed under the provisions of 35 U.S.C. § 112 (f) unless the element is expressly recited using the phrase "means for" or, in the case of a method, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Brief Description of the Drawings, and Claims of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims s reflect, inventive subject matter lies in less than all features of a single disclosed configuration or operation. The following claims are hereby incorporated into the Detailed Description, with each claims standing on its own to represent separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

Certain embodiments of the disclosure are encompassed in the claims presented at the end of this specification, or in other claims presented at a later date. Additional embodiments are encompassed in the following set of numbered embodiments:

Embodiment 1. A system, comprising:
   a pressurizing element;
   an atrial positioning structure coupled to the pressurizing element and configured to position the pressurizing element in a left atrium of a heart of a patient; and
   control circuitry configured to:
      operate the pressurizing element to decrease a pressure in the left atrium during atrial diastole to draw oxygenated blood out of the lungs of the patient by increasing left atrial reservoir strain and a relative volume of the left atrium to reduce a filling pressure in the left atrium; and
      operate the pressurizing element to increase the pressure in the left atrium during atrial systole to increase active strain by reducing a relative volume of the left atrium to increase a left atrial pressure during atrial systole, wherein the increase in the left atrial pressure during atrial systole increases a pressure differential between the left atrium and left ventricle that improves diastolic filling of the left ventricle.

Embodiment 2. The system of Embodiment 1, wherein the pressurizing element comprises a balloon, wherein operating the pressurizing element to increase the pressure in the left atrium comprises filling the balloon with a liquid or a gas, and wherein operating the pressurizing element to decrease the pressure in the left atrium comprises removing the liquid or the gas from the balloon.

Embodiment 3. The system of Embodiment 2, wherein the atrial positioning structure comprises a septal anchor or a left atrial appendage anchor.

Embodiment 4. The system of Embodiment 3, further comprising pressurizing components that include a pressure chamber and at least one pump disposed between the balloon and the pressure chamber.

Embodiment 5. The system of Embodiment 4, wherein the pressurizing components are configured to be external fixed, external ambulatory, or implantable components.

Embodiment 6. The system of Embodiment 3, wherein the atrial positioning structure comprises the septal anchor, wherein the septal anchor comprises first and second expandable members configured to expand respectively against left and right sides of an atrial septum of the heart of the patient, and wherein the balloon is attached to the first expandable member.

Embodiment 7. The system of Embodiment 6, wherein the pressurizing element comprises a turbine.

Embodiment 8. The system of Embodiment 1, wherein the pressurizing element comprises a pump.

Embodiment 9. The system of Embodiment 1, wherein the pressurizing element, when operated, causes a volume displacement in the left atrium.

Embodiment 10. A method, comprising:

deflating a balloon disposed in a left atrium of a heart of a patient to decrease a pressure in the left atrium during atrial diastole to draw oxygenated blood out of the lungs of the patient by increasing left atrial reservoir strain and a relative volume of the left atrium to reduce a filling pressure in the left atrium; and inflating the balloon to increase the pressure in the left atrium during atrial systole to increase active strain by reducing a relative volume of the left atrium to increase a left atrial pressure during atrial systole, wherein the increase in the left atrial pressure during atrial systole increases a pressure differential between the left atrium and left ventricle that improves diastolic filling of the left ventricle.

Embodiment 11. The method of Embodiment 10, wherein deflating the balloon comprises:

receiving, at control circuitry from a sensor communicatively coupled to the patient, a signal corresponding to a cardiac cycle for the heart of the patient; and deflating the balloon responsive to a portion of the signal.

Embodiment 12. The method of Embodiment 11, wherein inflating the balloon comprises inflating the balloon responsive to an additional portion of the signal.

Embodiment 13. The method of Embodiment 12, wherein the sensor comprises an electrical sensor or a pressure sensor.

Embodiment 14. A system, comprising:

a first pressurizing element;

an atrial positioning structure coupled to the first pressurizing element and configured to position the first pressurizing element in a left atrium of a heart of a patient;

a second pressurizing element;

a pulmonary artery positioning structure coupled to the second pressurizing element and configured to position the second pressurizing element in a pulmonary artery of the patient; and control circuitry configured to operate the first and second pressurizing elements to generate coordinated pressure modifications in the left atrium and the pulmonary artery.

Embodiment 15. The system of Embodiment 14, further comprising at least one sensor configured to sense a portion of a cardiac cycle for the patient, and wherein the control circuitry is configured to operate the first and second pressurizing elements to generate the coordinated pressure modifications responsive to a signal from the sensor.

Embodiment 16. The system of Embodiment 15, wherein the coordinated pressure modifications comprise a pressure change in the left atrium by operation of the first pressurizing element responsive to the signal and a pressure change in the pulmonary artery by the second pressurizing element based on the operation of the first pressurizing element.

Embodiment 17. The system of Embodiment 16, wherein the coordinated pressure modifications comprise reversing the pressure change in the left atrium with the first pressurizing element at a predetermined time after the pressure change by the first pressurizing element.

Embodiment 18. The system of Embodiment 16, wherein the coordinated pressure modifications comprise reversing the pressure change in the left atrium with the first pressurizing element responsive to an additional signal from the at least one sensor.

Embodiment 19. The system of Embodiment 15, wherein the coordinated pressure modifications comprise causing a pressure change in the left atrium with the first pressurizing element responsive to the signal and causing a pressure change in the pulmonary artery with the second pressurizing element responsive to an additional signal from the at least one sensor.

Embodiment 20. The system of Embodiment 19, wherein the coordinated pressure modifications comprise reversing the pressure change in the left atrium with the first pressurizing element at a predetermined time after the pressure change by the first pressurizing element.

Embodiment 21. The system of Embodiment 19, wherein the coordinated pressure modifications comprise reversing the pressure change in the left atrium with the first pressurizing element responsive to a further additional signal from the at least one sensor.

Embodiment 22. The system of Embodiment 15, wherein the coordinated pressure modifications comprise, during the cardiac cycle with the first pressurizing element, generating two pressure-increase periods separated by a pressure-decrease period that is longer than either of the two pressure-increase periods.

Embodiment 23. The system of Embodiment 21, wherein the coordinated pressure modifications comprise, during the cardiac cycle with the second pressurizing element, generating a pressure-decrease period, and a pressure-increase period that is longer than the pressure-decrease period.

Embodiment 24. The system of Embodiment 21, wherein the pressure-decrease period for the first pressurizing element and the pressure-increase period for the second pressurizing element are offset in time and extend for a common amount of time.

Embodiment 25. The system of Embodiment 15, wherein the at least one sensor comprises an electrical sensor configured to sense an electro-cardio signal in the patient.

Embodiment 26. The system of Embodiment 15, wherein the at least one sensor comprises at least one pressure sensor configured to sense a cardio-pulmonary pressure of the patient.

Embodiment 27. The system of Embodiment 26, wherein the at least one pressure sensor comprises a first pressure sensor in or near the left atrium and a second pressure sensor in or near the pulmonary artery.

Embodiment 28. The system of Embodiment 14, wherein the first pressurizing element comprises a first balloon and the second pressurizing element comprises a second balloon.

Embodiment 29. The system of Embodiment 28, further comprising pressurizing components that include a pressure chamber and at least one pump disposed between the first and second balloons and the pressure chamber.

Embodiment 30. The system of Embodiment 29, wherein the control circuitry is configured to operate the pressurizing components to generate the coordinated pressure modifications with the first and second pressurizing elements by:

triggering deflation of the second balloon responsive to detection of an R peak in an electro-cardiogram signal for a cardiac cycle for the patient;

triggering deflation of the first balloon following a first time delay after the detection of the R peak;

triggering inflation of the second balloon responsive to detection of a T peak in the electro-cardiogram signal for the cardiac cycle for the patient; and triggering inflation of the first balloon following a second time delay after the R peak.

Embodiment 31. The system of Embodiment 30, wherein the first time delay is between 90 milliseconds and 110 milliseconds, and wherein the second time delay is between 500 milliseconds and 700 milliseconds.

Embodiment 32. The system of Embodiment 30, wherein the deflation of the second balloon responsive to the detection of the R peak coincides with an opening of a pulmonary valve of the heart of the patient and a beginning of systole.

Embodiment 33. The system of Embodiment 32, wherein the inflation of the second balloon responsive to the detection of the T peak coincides with a closing of the pulmonary valve of the heart of the patient and a beginning of diastole.

Embodiment 34. The system of Embodiment 33, wherein the deflation of the first balloon coincides with a natural expansion and reservoir function phase of a left atrial cycle which occurs during ventricular systole when a mitral valve of the heart of the patient is closed.

Embodiment 35. The system of Embodiment 34, wherein the inflation of the first balloon coincides with atrial systole at an end of ventricular diastole before the mitral valve closes.

Embodiment 36. The system of Embodiment 35, wherein the inflation of the first balloon increases an atrial-ventricular pressure differential and increases ventricular filling for a left ventricle of the heart of the patient.

Embodiment 37. The system of Embodiment 29, wherein the control circuitry is configured to operate the pressurizing components to generate coordinated pressure modifications with the first and second pressurizing elements by operating the pressurizing components to:

deflate the second balloon during pulmonary artery systole to reduce pulmonary artery systolic pressures and reduce a work load of a right ventricle of the heart of the patient;

inflate the second balloon during pulmonary artery diastole after a pulmonary valve is closed to increase pulmonary artery diastolic pressure to overcome pulmonary vascular resistance and increase cardiac output;

deflate the first balloon during atrial diastole to draw oxygenated blood out of the lungs of the patient by increasing left atrial reservoir strain and a relative volume of the left atrium to reduce a filling pressure in the left atrium; and inflate the first balloon during atrial systole to increase active strain by reducing a relative volume of the left atrium to increase a left atrial pressure during atrial systole.

Embodiment 38. The system of Embodiment 37, wherein the increase in the left atrial pressure during atrial systole increases a pressure differential between the left atrium and left ventricle that improves diastolic filling of the left ventricle.

Embodiment 39. The system of Embodiment 29, wherein the pressurizing components are configured to be external fixed, external ambulatory, or implantable components.

Embodiment 40. The system of Embodiment 14, wherein the first pressurizing element or the second pressurizing element comprises a turbine.

Embodiment 41. The system of Embodiment 14, wherein the first pressurizing element or the second pressurizing element comprises a pump.

Embodiment 42. The system of Embodiment 14, wherein the atrial positioning structure comprises a septal anchor configured for attachment to a septum of the heart of the patient.

Embodiment 43. The system of Embodiment 14, wherein the atrial positioning structure comprises a left atrial appendage anchor or an anchoring member configured for anchoring in an orifice of one or more pulmonary veins.

Embodiment 44. The system of Embodiment 14, wherein the pulmonary artery positioning structure comprises an expandable cage disposed in-line with the second pressurizing element.

Embodiment 45. The system of Embodiment 14, wherein the first pressurizing element, when operated, causes a volume displacement in the left atrium.

Embodiment 46. The system of Embodiment 45, wherein the second pressurizing element, when operated, causes a volume displacement in the pulmonary artery.

Embodiment 47. A method, comprising:

inflating a first balloon in a left atrium of a patient during a first portion of each of multiple cardiac cycles for the patient;

inflating a second balloon in a pulmonary artery of the patient during a second portion of each of the cardiac cycles;

deflating the first balloon during a third portion of each of the cardiac cycles; and deflating the second balloon during a fourth portion of each of the cardiac cycles.

Embodiment 48. The method of Embodiment 47, wherein the third portion and the fourth portion partially overlap, wherein the first portion and the second portion partially overlap, and wherein the second portion and the third portion partially overlap.

Embodiment 49. A system, comprising:

a first implantable fluid-displacement element;

a first positioning structure coupled to the first implantable fluid-displacement element and configured to position the first implantable fluid-displacement element in fluid communication with a portion of a left side of a heart of a patient;

a second implantable fluid-displacement element;

a second positioning structure coupled to the second implantable fluid-displacement element and configured to position the second implantable fluid-displacement element in fluid communication with a portion of a right side of the heart; and control circuitry configured for coordinated operation of the first and second implantable fluid-displacement elements during each cardiac cycle of the heart.

Embodiment 50. The system of Embodiment 49, wherein the first implantable fluid-displacement element comprises at least one of a pressurizing element and a volume-displacement element.

Embodiment 51. The system of Embodiment 50, wherein the second implantable fluid-displacement element comprises at least one of a pressurizing element and a volume-displacement element.

Embodiment 52. The system of Embodiment 49, wherein the first positioning structure is configured to position the first implantable fluid-displacement element in a left atrium of the heart.

Embodiment 53. The system of Embodiment 52, wherein the second positioning structure is configured to position the second implantable fluid-displacement element in a pulmonary artery of the patient or a right ventricle of the heart of the patient.

Embodiment 54. The system of Embodiment 49, wherein the first and second implantable fluid-displacement elements each comprise at least one of a balloon, a pump, or a turbine.

Embodiment 55. The system of Embodiment 49, wherein the control circuitry is configured to operate the first and second implantable fluid-displacement elements responsive to at least one sensor signal from a sensor that detects portions of the cardiac cycle.

What is claimed is:

1. A method comprising:

inserting a lumen through a right atrium of a heart, across an interatrial septum, and into a right ventricle of the heart, the lumen in fluid communication with a pressurizing element;

anchoring an anchoring structure within a pulmonary artery of the heart, the anchoring structure coupled to the lumen; and operating the pressurizing element to increase and decrease a relative volume of the right ventricle by increasing and decreasing a pressure within the pressurizing element over multiple cardiac cycles.

2. The method of claim 1, wherein the anchoring structure comprises an expandable mesh structure.

3. The method of claim 1, wherein increasing and decreasing the pressure within the pressurizing element is based on signals received from one or more pressure sensors.

4. The method of claim 1, wherein increasing and decreasing the pressure within the pressurizing element is based on signals received from one or more electrocardiogram sensors.

5. The method of claim 1, wherein operating the pressurizing element to increase the relative volume of the right ventricle is timed to coincide with at least one of diastole or systole.

6. The method of claim 1, wherein operating the pressurizing element comprises filling the pressurizing element with a liquid or a gas and removing the liquid or the gas from the pressurizing element.

7. The method of claim 1, wherein the pressurizing element is in fluid communication with a pump, the pump configured to supply fluid to the pressurizing element.

8. The method of claim 7, wherein the pressurizing element is in fluid communication with a second pump, the second pump configured to remove fluid from the pressurizing element.

9. The method of claim 7, wherein the pump is housed in a wearable external portable unit.

10. The method of claim 7, wherein the pump is configured to supply fluid to a pressure reservoir in fluid communication with the pressurizing element.

11. The method of claim 7, wherein operation of the pump is controllable by a control system.

12. The method of claim 11, wherein the control system is configured to control at least one of: a volume of fluid delivered to the pressurizing element or a duration of fluid delivery to the pressurizing element.

13. The method of claim 11, wherein the control system is electrically connected to a user interface, the user interface configured to control operation of the pressurizing element.

14. The method of claim 10, wherein a valve is connected to a fluid line between the pressure reservoir and the pressurizing element.

15. The method of claim 14, wherein a control system actuates the valve in response to signals received from one or more electrocardiogram sensors or one or more pressure sensors.

16. The method of claim 1, wherein the pressurizing element comprises a balloon.

17. The method of claim 1, wherein the pressurizing element is oval shaped.

18. The method of claim 1, wherein the pressurizing element comprises an anti-thrombotic material.

19. The method of claim 1, wherein the pressurizing element comprises a volume-displacement mechanism.

20. A method comprising:

inserting a lumen through a right atrium of a heart, across an interatrial septum, and into a right ventricle of the heart, the lumen in fluid communication with a pressurizing element;

anchoring an anchoring structure within a pulmonary artery of the heart, the anchoring structure coupled to the lumen; and operating the pressurizing element to reduce work required of the right ventricle by increasing and decreasing a pressure within the pressurizing element over multiple cardiac cycles.

* * * * *